US012478759B1

(12) United States Patent
Mitchell

(10) Patent No.: US 12,478,759 B1
(45) Date of Patent: Nov. 25, 2025

(54) THERAPEUTIC VIBRATION DEVICE AND METHOD OF USE THEREOF

(71) Applicant: Charlie B. Mitchell, Brentwood, TN (US)

(72) Inventor: Charlie B. Mitchell, Brentwood, TN (US)

( * ) Notice: Subject to any disclaimer, the term of this patent is extended or adjusted under 35 U.S.C. 154(b) by 636 days.

(21) Appl. No.: 17/982,762

(22) Filed: Nov. 8, 2022

Related U.S. Application Data

(63) Continuation-in-part of application No. 15/908,067, filed on Feb. 28, 2018, now abandoned.

(51) Int. Cl.

| | |
|---|---|
| ***A61M 21/00*** | (2006.01) |
| ***A61M 16/06*** | (2006.01) |
| ***H04R 1/02*** | (2006.01) |
| ***H04R 3/00*** | (2006.01) |

(52) U.S. Cl.
CPC ........ *A61M 21/00* (2013.01); *A61M 16/0683* (2013.01); *H04R 1/028* (2013.01); *H04R 3/00* (2013.01); *A61M 2021/0022* (2013.01); *A61M 2021/0027* (2013.01); *A61M 2205/07* (2013.01); *A61M 2205/3592* (2013.01); *A61M 2210/0693* (2013.01)

(58) Field of Classification Search
CPC .................. A61H 23/02; A61H 47/006; A61H 2007/009; A61H 9/005; A61H 2201/1604; A61H 2205/02; A61M 21/00
See application file for complete search history.

(56) References Cited

U.S. PATENT DOCUMENTS

2017/0135894 A1* 5/2017 Jones, Jr. ............... A61H 7/006

FOREIGN PATENT DOCUMENTS

CN 107669460 A * 2/2018 ............... A61N 2/06
CN 113397814 A * 9/2021 ............. A61F 9/045

* cited by examiner

*Primary Examiner* — Kendra D Carter
*Assistant Examiner* — Jaeick Jang
(74) *Attorney, Agent, or Firm* — Patterson Intellectual Property Law, P.C.; Mark A. Kilgore

(57) ABSTRACT

A therapeutic vibration device includes a body with at least a first vibration element connected to the body, and at least a second vibration element connected to the body. Additionally, at least one audio transducer may be connected to the body. The first vibration element and second vibration element may have vibration characteristics which are different from each other when compared. Additionally, the device may include a controller that is connected to a user input interface which allows the user to control the vibration elements.

18 Claims, 19 Drawing Sheets

THERAPEUTIC VIBRATION DEVICE AND METHOD OF USE THEREOF

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

CROSS-REFERENCES TO RELATED APPLICATIONS

This application claims benefit of the following patent application(s) which is/are hereby incorporated by reference: U.S. patent application Ser. No. 15/908,067 filed on Feb. 28, 2018.

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND

The present disclosure relates generally to a device used as part of an alternative healing plan for pain, brain injuries, and neurological disorders. More particularly, the disclosure pertains to therapeutic devices that use vibrations to provide relief from a traumatic head injury. When used in conjunction with physical exercise, supplements, brain exercises, and other holistic regimens, the user may increase blood flow circulation, stimulate the brain, help in restoring the brain to a pre-injury state, and help reduce recovery time after future injuries.

The prior art recognizes the therapeutic effects that vibration stimuli have on individuals. The use of vibration therapy can be localized to a particular part of the body, such as the arm, leg, back, neck, or head, or can also be applied to the entire body, known as whole-body vibration. For localized applications, studies have shown beneficial effects for a person suffering from acute pain when treated with localized vibration therapy. The mechanisms of therapeutic action are still not fully understood, but the effectiveness has been shown under certain conditions. Likewise, whole-body vibration has shown to have therapeutic effects including increased circulation, reduced pain, reduced fatigue, and a decrease in stress levels.

Traumatic brain injury (TBI) occurs when an external force is exerted on an individual which causes the brain to move rapidly inside the skull. External forces such as automobile accidents, falls, or contact sports, may result in such injury. Non-traumatic brain injury is the result of a medical disease or process that results in impairments to the brain. Diseases such as strokes, tumors, Alzheimer's, or dementia, can result in non-traumatic brain injury.

Considering mild traumatic brain injuries, such as concussions, rest is one of the most common treatments to allow an individual's brain to recover. Both physical and mental rest is advised so as to avoid activities that may increase, or further aggravate, any symptoms of the injury. As symptoms of the injury resolve, more activity may be enjoyed so long as the symptoms do not worsen. In addition to rest, pain relievers such as acetaminophen may be taken. Further alternative treatment options that aid in recovery from a mild traumatic brain injury are needed to provide additional opportunities to help shorten the recovery time, or help in restoring the brain to a more complete pre-injury state.

BRIEF SUMMARY

The present disclosure relates, in one embodiment, to a therapeutic vibration device. The therapeutic vibration device may include a body. The device may also include at least one first vibration element connected to the body and may also include at least one second vibration element connected to the body. The second vibration element may be configured to operate differently from the first vibration element. At least one audio transducer may be connected to the body. The body of the therapeutic vibration device may include a helmet. The body of the therapeutic vibration device may alternatively include a headband.

In one embodiment, a controller may be electrically coupled to at least one first vibration element and to at least one second vibration element. The controller may be communicatively connected to a user input interface. The user input interface may be disposed on the body or may be remote from the body. The user input interface may also include at least one selector. The user input interface may be coupled to the controller via a wired or wireless connection.

In other embodiments, the vibration device may have at least one first vibration element which is configured to operate with a first vibration characteristic. The device may also have at least one second vibration element which is configured to operate with a second vibration characteristic. The first characteristic may be different from the second vibration characteristic in some embodiments.

In one embodiment, the vibration device may include a first vibration characteristic which is configured to operate for a longer duration than the second vibration element.

In another embodiment, the vibration device may include a CPAP mask which may be connected to the body of the device.

The present disclosure may also relate to an embodiment having a body with at least one flexible bladder configured to be filled with a fluid that is connected to the body. Additionally, the device may have at least one vibration element disposed between the body and the flexible bladder. The fluid used to fill the bladder may be a gas.

The device may include a pump that is fluidly connected to the flexible bladder wherein the pump may be configured to at least partially fill the flexible bladder with the fluid. The pump may be electrically operated and the pump may be electrically coupled to a controller. The pump may include a two-way pump.

In one embodiment, the body may include a helmet which may be connected to the flexible bladder. In another embodiment, the body may include a headband connected to the flexible bladder.

In an embodiment, the present disclosure also relates to a method including activating at least one first vibration element connected to a helmet. The vibration element may have a first vibration characteristic. Additionally, the disclosure relates to a method including activating at least one audio transducer connected to the helmet, wherein the audio transducer is operated independently of the first vibration element.

The method may include activating at least one first vibration element connected to a helmet as part of an alternative healing regimen for a concussion sustained by the user. The method may include activating at least one first vibration element connected to a helmet as part of an alternative healing regimen for a user having a neurodegenerative disorder. The method may include activating an audio transducer to sound an alarm to notify the user at a designated time of an occurrence of an event. The method may include activating an audio transducer to play music.

Finally, the method may include activating at least one second vibration element connected to the helmet, wherein the at least one second vibration element has a second vibration characteristic. The second vibration characteristic may be different from the first vibration characteristic.

DETAILED DESCRIPTION

Figure 1:
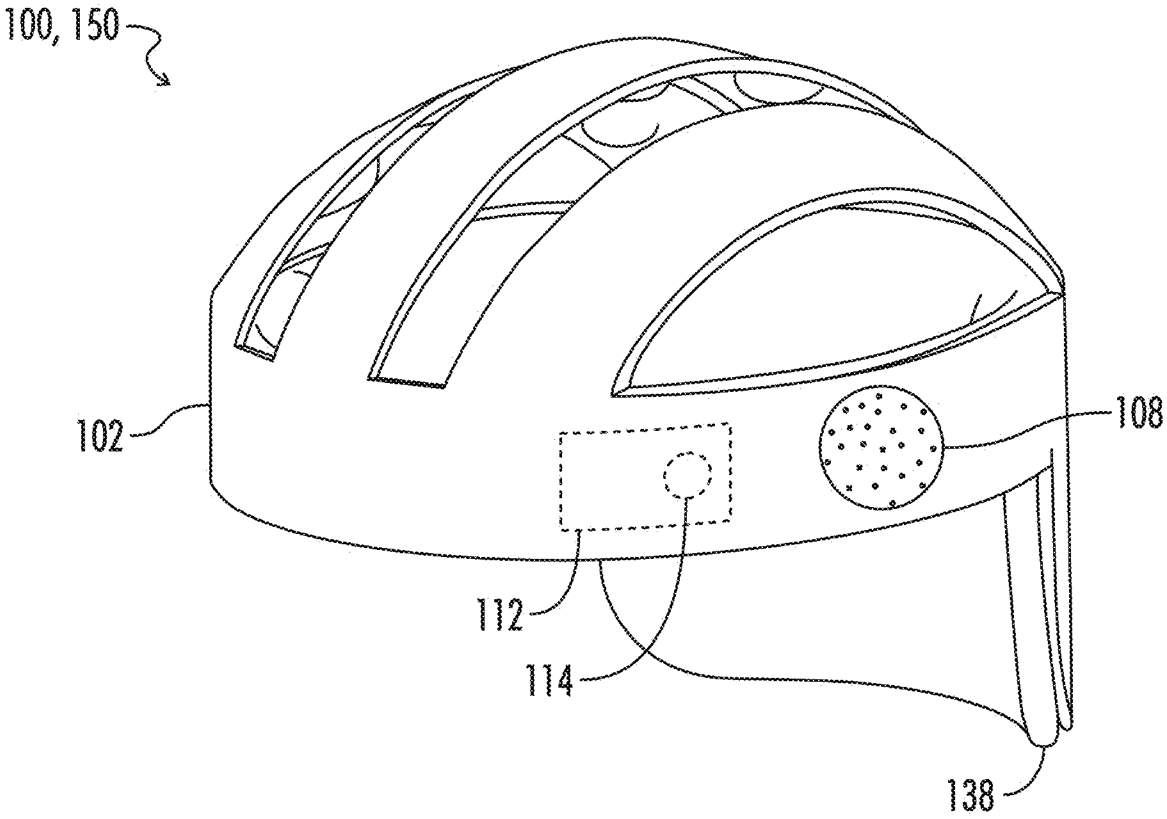
FIG. 1 is a perspective view of an embodiment of a therapeutic vibration device as a helmet.

Reference will now be made in detail to embodiments of the present disclosure, one or more drawings of which are set forth herein. Each drawing is provided by way of explanation of the present disclosure and is not a limitation. In fact, it will be apparent to those skilled in the art that various modifications and variations can be made to the teachings of the present disclosure without departing from the scope of this disclosure. For instance, features illustrated or described as part of one embodiment can be used with another embodiment to yield a still further embodiment.

Thus, it is intended that the present disclosure covers such modifications and variations as come within the scope of the appended claims and their equivalents. Other objects, features, and aspects of the present disclosure are disclosed in, or are obvious from, the following detailed description. It is to be understood by one of ordinary skill in the art that the present discussion is a description of exemplary embodiments only and is not intended as limiting the broader aspects of the present disclosure.

The meanings identified below do not necessarily limit the terms, but merely provide illustrative examples for the terms. The meaning of "a", "an", and "the" may include plural references, and the meaning of "in" may include "in" and "on". The phrase "in one embodiment", as used herein does not necessarily refer to the same embodiment, although it may. The meaning of "or" may include "and" and "or".

The term "coupled" means at least either a direct electrical connection between the connected items or an indirect connection through one or more passive or active intermediary devices.

The term "controller" as used herein may refer to, be embodied by, or otherwise include within a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed and programmed to perform or cause the performance of the functions described herein. A general purpose processor can be a microprocessor, but in the alternative, the processor can be a microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration.

Conditional language used herein, such as, among others, "can", "might", "may", "e.g.", and the like, unless specifically stated otherwise, or otherwise understood within the context as used, is generally intended to convey that certain embodiments include, while other embodiments do not include, certain features, elements, and/or states. Thus, such conditional language is not generally intended to imply that features, elements, and/or states are in any way required for one or more embodiments or that one or more embodiments necessarily include logic for deciding, with or without user input or prompting, whether these features, elements, and/or states are included or are to be performed in any particular embodiment.

The term "user input interface" as used herein may, unless otherwise stated, include any input-output module including, but not limited to, a device having a selector such as a button, switch, lever, dial, adjuster, knob, toggle, or the like, which, when used, sends a signal from the interface to the controller. Additionally, the "user-input interface" may also include, but is not limited to, a digital touch screen, web portal, such as individual web pages or those collectively defining a hosted website, mobile device applications, telephony interfaces such as interactive voice response, and the like.

The term "fluid" as used herein may, unless otherwise stated, include any substance that has no fixed shape including, but not limited to, a gas, liquid, semi-liquid, plasma, or any other substance that deforms under an applied shear stress.

The term "therapy" and "therapeutic" as used herein may, unless otherwise stated, include any treatment, device, behavior, regimen, intervention, remedy, and the like, to help a person feel better physically, emotionally, mentally, or otherwise from the effects of a disease or injury. Therapy may include medical treatments, but may also include holistic treatments that may be administered by the individual user or a third party.

The particular disclosure provided herein pertains to the use of alternative healing to neurological disorders, as well as traumatic and non-traumatic injuries of the brain. Vibration therapy has been shown to help increase the production of hormones associated with exercise as well as depress the response of hormones associated with stress. Pathways such as neurogenesis are thought to be involved in the beneficial effects seen through vibration therapy. Additionally, the mechanism of vibration therapy may help improve circulation through increasing the speed of blood flow. The repeated use of vibration therapy may allow for an increased supply of nutrients and oxygen rich blood to reach the brain which aids in recovery of the injury. The production of beneficial hormones and pathways such as neurogenesis not only create new neurons, but also protect existing neurons as well as the communication between them.

The neuroplasticity of a brain refers to the brain's ability, in some instances, to undergo cortical remapping in response to injury. Rehabilitation of brain injury victims, which may include activation of neuroplasticity through cortical remapping, has provided improvements in functional outcomes after injury. The use of vibration therapy in concert with other alternative healing regimens may increase functional outcomes of patients after suffering a brain injury. Further, the addition of vibration therapy may reduce recovery time and allow an individual to resume activities, or work, in a shorter amount of time. Finally, vibration therapy may provide a mechanism to restore the brain to its original, pre-injury state and thus allow the individual to resume life, at least in a cognitive sense, to before the injury occurred.

Figure 2:
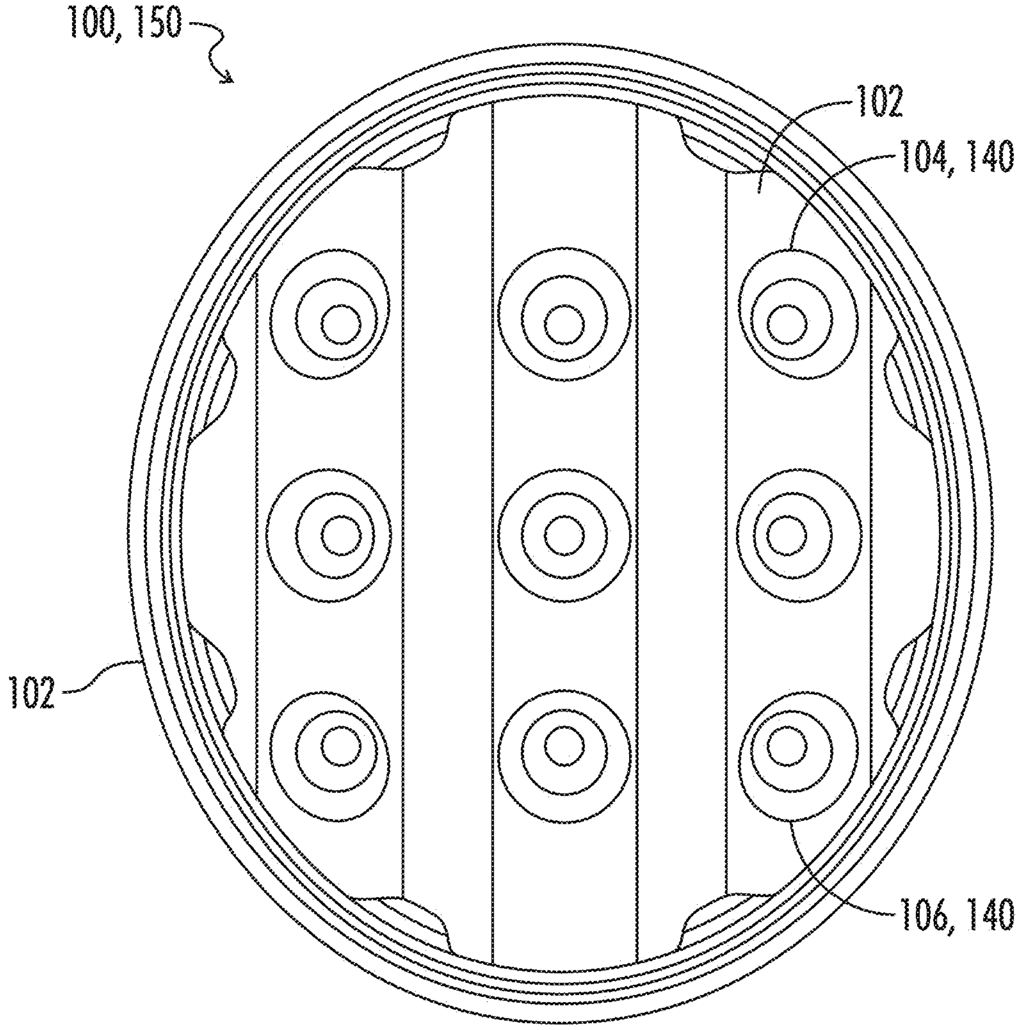
FIG. 2 is a bottom view of the therapeutic vibration device of FIG. 1 illustrating embodiments of the vibration elements.

Referring initially to FIGS. 1 and 2, a therapeutic vibration device 100 may have a body 102 with at least a first vibration element 104 connected to the body 102, and at least a second vibration element 106 connected to the body 102. Additionally, at least one audio transducer 108 may be connected to the body 102. In some embodiments, the audio transducer 108 may be an audio speaker used to generate white noise which may be soothing to a user, or may be used to help a user fall asleep. The use of white noise is not limiting, but may be used for any means the user or a third party desires. A third party may include a therapist, doctor, nurse, or other party administering or providing the therapeutic services to the user.

In additional embodiments, the audio transducer 108 may be used to play music or other audible sound that is selected by the user or is determined by a third party. In other embodiments, the audio transducer 108 may be used to generate audible tones to notify the user at a designated time of an occurrence of an event, such as, a designated time to change the settings of the vibration elements. Another embodiment may include the audio transducer 108 used to play a tone to designate a time for the user to take medication associated with the holistic therapy regimen.

Referring now to FIGS. 1-2, and FIGS. 7-9, various embodiments are shown pertaining to the body 102. In one embodiment, the body 102 may be or include a helmet 150. In another embodiment, the body 102 may be or include a head band 152. Alternatively, the body 102 may be or include a cap. The body 102 may be made of any appropriate material, such as leather. In other embodiments, the body 102 may be made, in whole or in part, of metals, polymers, fabrics, or other suitable materials.

Figure 3:
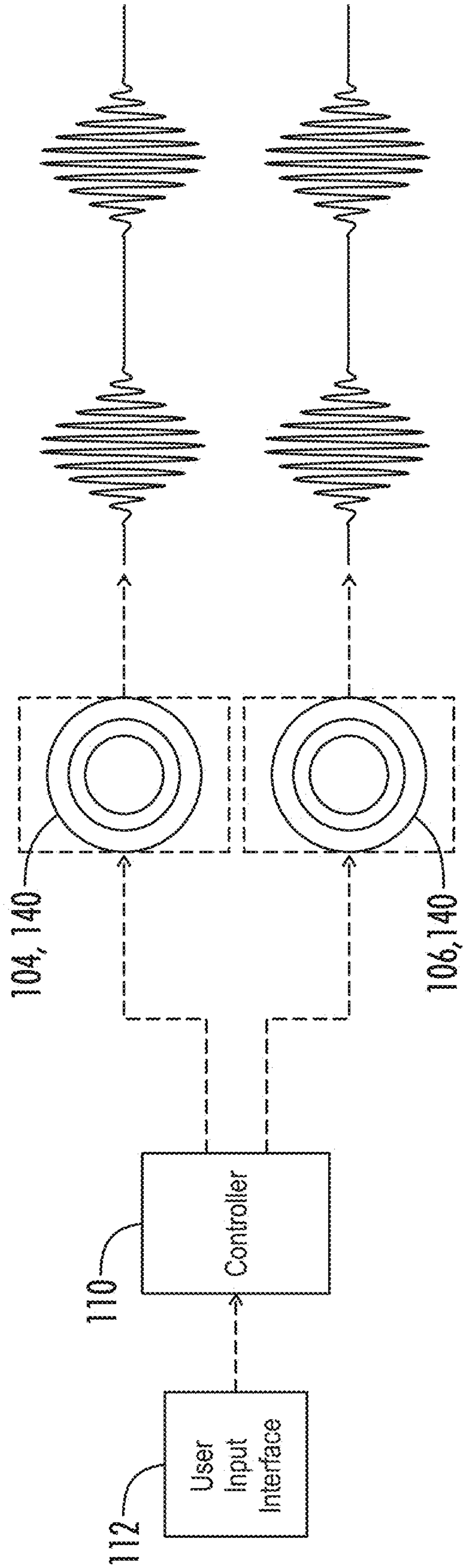
FIG. 3 is a block diagram representing an embodiment of a system for controlling a vibration element in accordance with the present disclosure.

Referring specifically now to FIG. 2, in some embodiments, the device 100 may contain at least one first vibration element 104 and at least one second vibration element 106, wherein each vibration element is disposed on the body 102. In some embodiments, the body 102 may contain nineteen (19) vibration elements. In other embodiments, the body 102 may contain any number of a plurality of vibration elements. In one particular embodiment, the first vibration element 104 and second vibration element 106 are connected to the underside of the body 102 so as to contact the user directly when the device is used. The plurality of vibration elements 104, 106 may be of an appropriate number such that the majority of a user's head may be within the therapeutic region of the vibrations being produced by the vibration elements. The coverage of the majority of the user's head will allow for designated points of vibration to target a specific region of the user's head for holistic therapy. Additionally, the vibration elements 104, 106 may be positioned in a way so as to target a specific region of the user's brain to provide relief from concussions, other brain injuries, or disease states. In some embodiments, a vibration mechanism may include a motor which serves to drive an eccentric rotating mass causing vibration. In such embodiments, the motor may include, for example, a 10 mm Iron-core DC motor with an associated eccentric mass. In other embodiments, the eccentric rotating mass may be the same on all vibrating mechanisms. In other embodiments, the eccentric mass may be different on some or all of the vibrating mechanisms. Likewise, in some embodiments, the vibration mechanism may include a piezoelectric mechanism Now also referring to FIGS. 1-3, in some embodiments, the first vibration element 104 and the second vibration element 106 may be operated by a controller 110. The controller 110 may be used to operate the various vibration elements 104, 106 either in unison or may operate them individually. In one embodiment, the controller 110 may be communicatively connected to a user input interface 112 which may allow a user to operate the vibration device 100. The user input interface 112 may be disposed on the body 102. In another embodiment, the user input interface 112 may be remote from the body 102 and may be wired or wirelessly coupled to the controller 110.

The user input interface 112 may also be provided via a mobile device or other user computing device such as a desktop, laptop, tablet, or the like. In one embodiment, the user input interface 112 may be accessed through a web portal such as a website. In an embodiment using a mobile device, the user may access the user input interface 112 through a mobile application. In some embodiments, the mobile application may control the vibration characteristics and the individual vibration elements 104, 106, as well as allow the user to control the audio transducer 108. For example, the mobile application, acting as the user input interface 112, may allow a user to select playlists, or individual songs that will be played through the audio transducer 108. Additionally, the mobile app may provide reminders to the user, such as when to start and/or stop the therapeutic session, when to change the vibration to a different area of the head, or when to change the mode of vibration that is being given. Further, the mobile app may provide audible, visual, or tactile reminders to take supplements, medication, or do exercise during, before, or after the treatment session.

In certain embodiments, the user input interface 112 may incorporate at least one selector 114 which allows the user to control the vibration elements 104, 106. In some embodiments, the user input interface 112 may include a selector 114 such as, but not limited to, a button, switch, lever, dial, adjuster, knob, toggle, or the like which allows the user to control the vibration elements 104, 106. The selector 114 may be used in a variety of ways to operate the vibration elements 104, 106, or to operate the vibration device 100 in whole, or in part. In one embodiment, the selector 114 may be used to turn the vibration elements on or off. In another embodiment, the selector 114 may select one vibration element to turn on or off independently from another vibration element.

Figure 4:
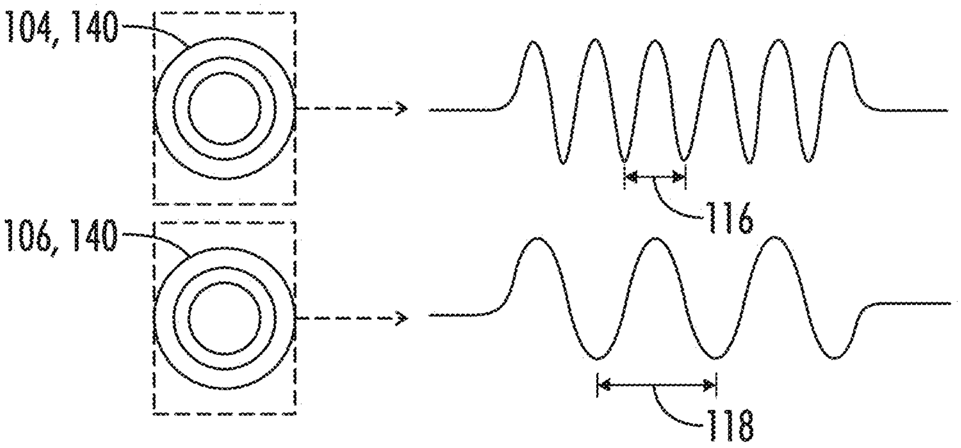
FIG. 4 is a block diagram representing an embodiment of vibrational elements illustrating differences in vibration frequency.
Figure 5:
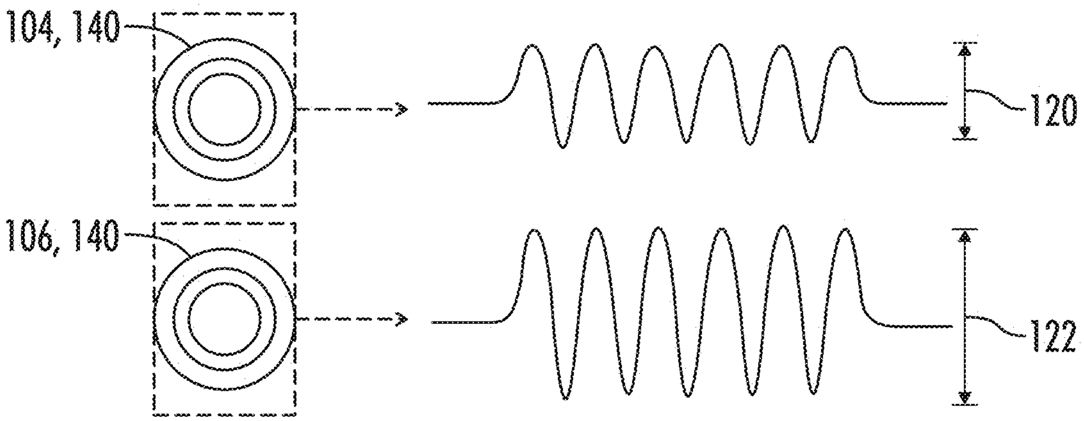
FIG. 5 is a block diagram representing an embodiment of vibrational elements illustrating differences in vibration amplitude.
Figure 6:
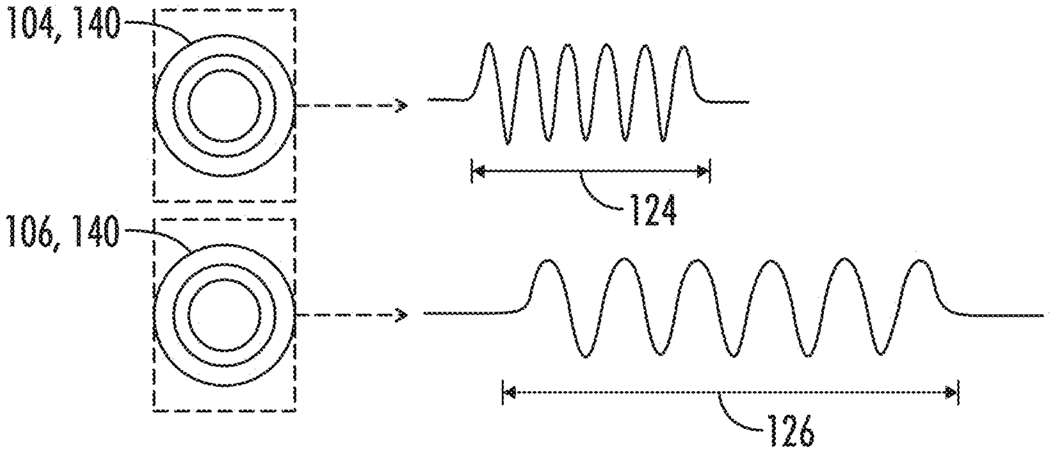
FIG. 6 is a block diagram representing an embodiment of vibrational elements illustrating differences in vibration duration.

In some embodiments, the selector 114 may change the vibration characteristics of the vibration elements 104, 106. These characteristics may include, for example, vibration frequency, amplitude, or duration. Referring to FIG. 4, the first vibration element 104 may have a first vibration frequency 116, and the second vibration element 106 may have a second vibration frequency 118, and when compared, the first and second vibration frequency may be different. Likewise, FIG. 5 provides the first vibration element 104 having a first vibration amplitude 120, and the second vibration element 106 having a second vibration amplitude 122, and when compared, the first and second vibration amplitudes may be different. In FIG. 6, the first vibration element 104 may have a first duration 124, and the second vibration element 106 may have a second duration 126, and when compared, the first and second vibration durations may be different.

In certain embodiments, the controller 110 may be used by the user to manipulate any one of the vibration characteristics. In one embodiment, the selector 114 may be used to adjust a single characteristic, such as frequency, amplitude, or duration for all vibration elements 104, 106. Alternatively, the selector 114 may be configured to adjust any one single characteristic for each individual vibration element independent of any other vibration element. This embodiment would allow a user to selectively adjust the vibration characteristics for more targeted therapeutic relief of a certain region of the user's head. For example, the selector 114 may allow a user to only turn on vibration elements on the left side of the device 100 so as to target the left side of the user's head or brain regions. This may also be done for any other region of the head, or may be done for multiple regions of the head at the same time. It will be apparent to a person having ordinary skill in the art that the use of the controller 110 and user input interface 112 to selectively apply various vibrational elements 104, 106, whether the selection includes the elements being on or off, or changing the characteristics of the vibration, will result in a vast number of possibilities which increase with greater number of vibration elements connected to the body 102.

In a specific embodiment having nineteen (19) vibration elements 104, 106 connected to the body 102, each vibration element is independently controlled by the user using the user input interface 112 which is communicatively connected to the controller 110. The user may select predetermined modes of vibration, or may independently select certain vibration characteristics to be applied through each vibration element 104, 106. The predetermined modes of vibration stored within the controller may include, but are not limited to, selecting a single targeted area of the head to receive therapeutic vibration, selecting multiple targeted areas of the head, or applying certain predetermined characteristics to all of the vibration elements 104, 106. Additionally, the user may independently select, or may select from predetermined modes, certain patterns of vibration that repeat so as to create an ongoing pattern of changing vibration characteristics. In one example, the user may select between three different settings, such as low, medium, and high, with the setting referring to the frequency or amplitude individually, or together. If the settings refer to the frequency rate, then the low, medium, and high frequencies are determined relative to each other. A user may select the first setting at a given frequency (low), or may select a second setting which has a higher frequency than the first (medium), or may yet select a third setting which has an even higher frequency than the first and second (high). Similarly, the same may be accomplished for amplitude in the same manner. Additionally, as noted before, the settings of low, medium, and high, may also correlate to both frequency and amplitude together, with a low setting including a given frequency and a given amplitude, with subsequent settings (medium, high) being greater than the preceding setting(s).

Likewise, the user may increase the frequency of a single vibration element 104, 106, all vibration elements, or any combination of vibration elements, and then may also decrease the frequency. This may be done in a repetitive pattern to create a wave of increasing and decreasing vibration frequency. Likewise, this pattern may also be stored as a mode in the controller 110 and the user may select a mode which provides the wave of increasing and decreasing vibration frequency. These patterns may also be used for other characteristics and is not limited to only a single characteristic. All characteristics may be changed one at a time, changed all together, or any combination thereof. The versatility of selecting a single vibration element 104, 106, or any combination of elements, along with selecting and modifying the characteristic of each vibration element allows for targeted holistic therapy to a specific region of the brain or head in order to help heal injuries such as concussion, or disease states such as dementia, amnesia, or insomnia.

Figure 7:
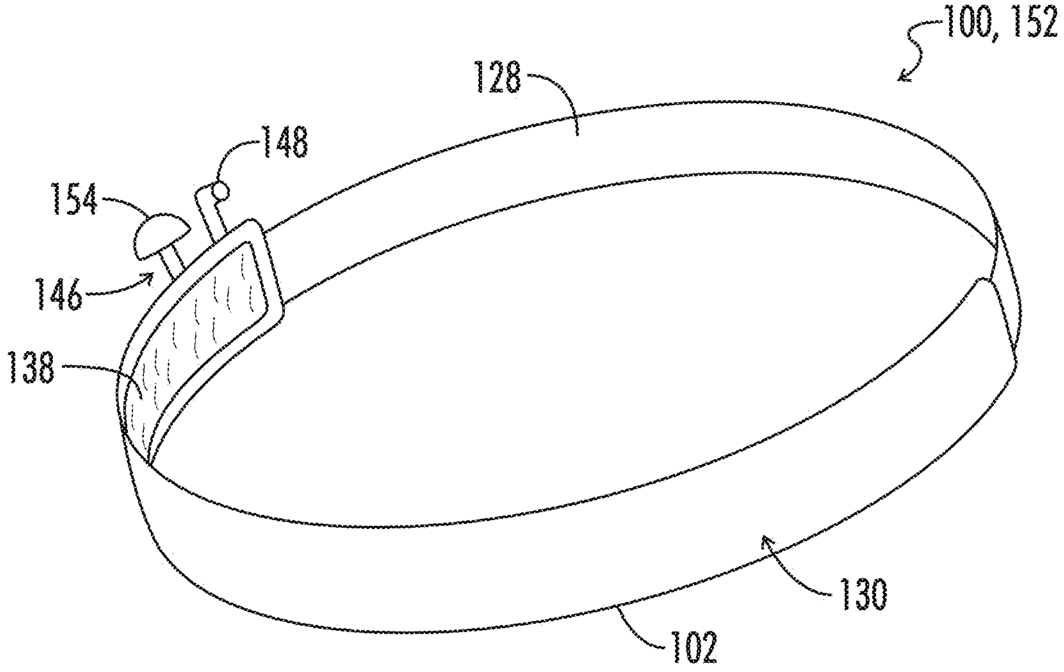
FIG. 7 is a perspective view of an embodiment of the therapeutic vibration device as a headband.
Figure 8:
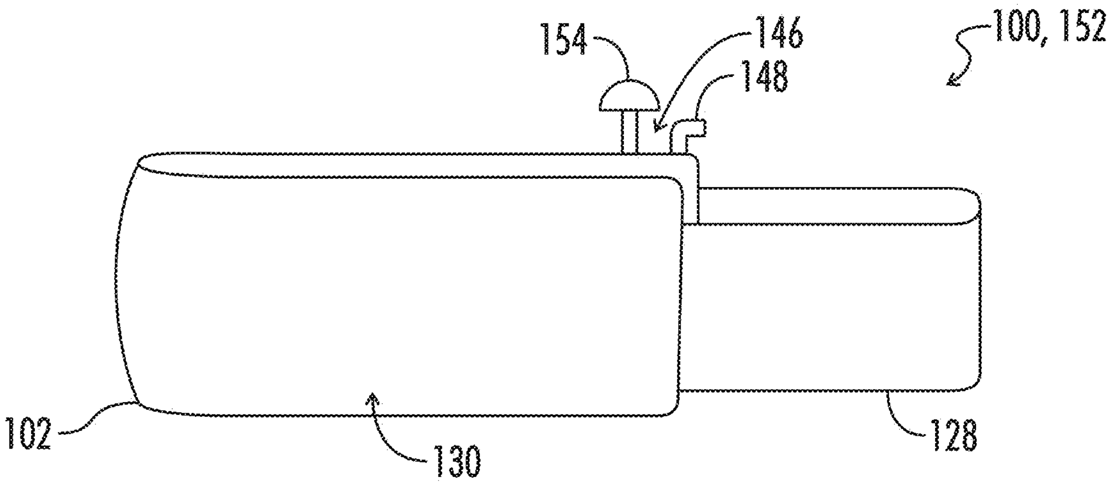
FIG. 8 is a side view of the therapeutic vibration device of FIG. 7.
Figure 9:
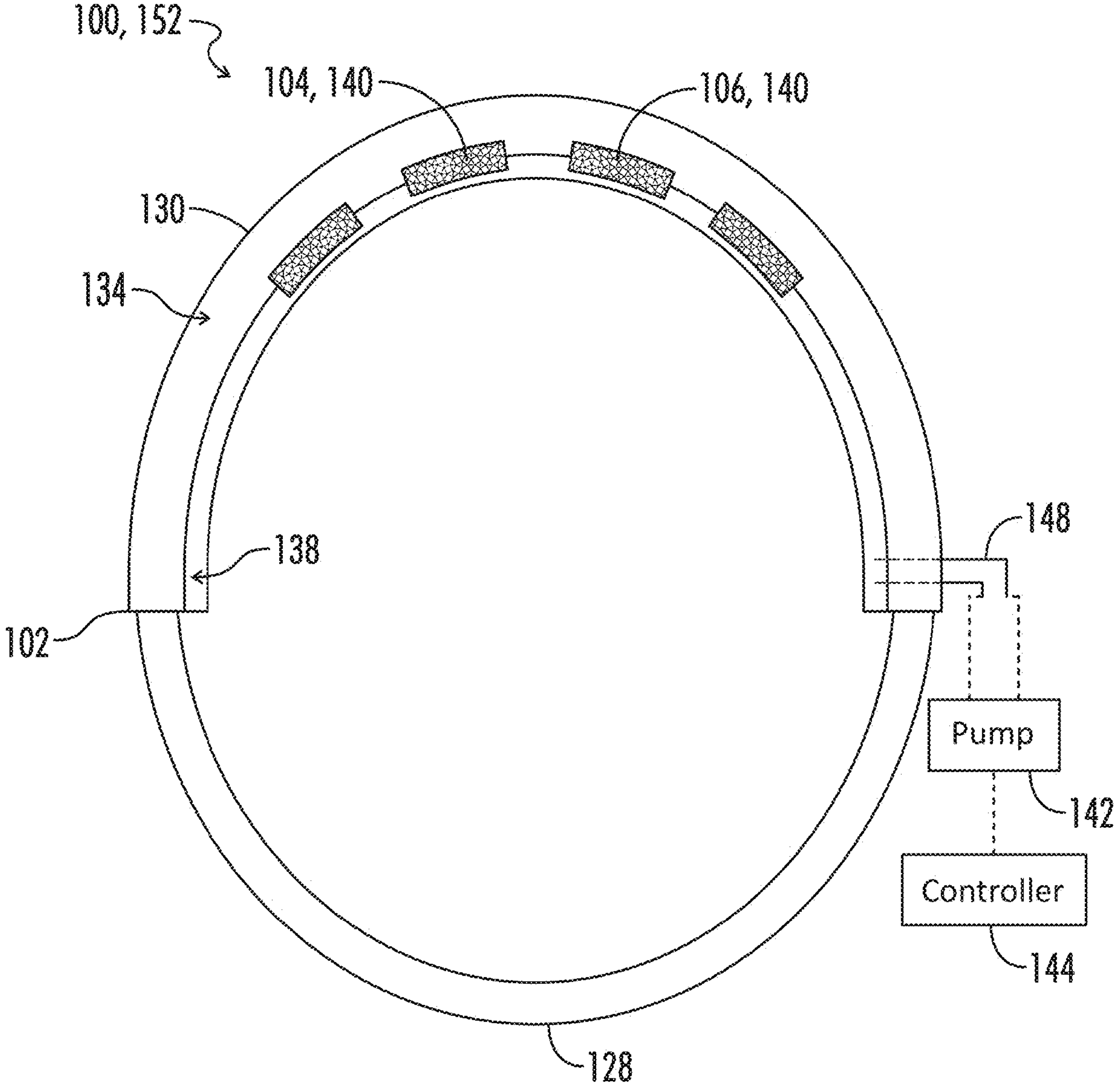
FIG. 9 is a top view of the therapeutic vibration device of FIG. 7.

Referring to FIGS. 7-9, the body 102 may include a headband 152 to be worn around a user's head. In one embodiment, the headband 152 may be secured to a user's head using an adjustable strap 128. The adjustable strap 128 may be made of material that stretches or may be made of material that is rigid. For example, the strap 128 may be made of Spandex, Lycra, polyurethane fabric, or the like to provide adjustability due to the inherent elasticity of the fabric. Likewise, the strap 128 may be formed from a material that has minimal elasticity such as cotton, denim, linen, leather, plastic, or similar materials. The strap 128 may be mounted permanently to the body 102. Alternatively, the strap 128 may be permanently mounted only to one side of the body 102 and then connected to the other side through a fastener mechanism, for example, but not limited to, a cinch strap, hook and loop, side release buckle, top release buckle, strap buckle, or the like. Additionally, the strap 128 may be removably mounted on both sides of the body 102 to allow the strap to be removed entirely which may facilitate replacement, washing, adjustment, and the like.

In one embodiment, the headband 152 may further include a housing 130. The housing 130 may include at least one vibration element 140. In another embodiment, the housing 130 may include an insulating layer 134 that is disposed between the housing 130 and the at least one vibration element 140. The insulating layer 134 may provide, for example, noise reduction due to the at least one vibration element 140. In some embodiments, the insulating layer may be chosen from the group comprising eva foam, polyethylene foam, polyurethane foam, rubber, neoprene, PVC, and the like.

In some embodiments, the headband 152 may be worn by a user so as to locate the body 102 on the user's forehead and the strap 128 used to secure the device by extending around the back of the user's head. Alternatively, the body 102 may be made of sufficiently flexible material so as to allow the headband 152 to be placed in any configuration so as to provide therapeutic relief to a targeted region of the user's head. For example, in one embodiment, the headband 152 may be placed so as to locate the body 102 on the side of a user's head, or on the rear of the user's head, so as to provide vibration therapy to those affected areas.

In some embodiments, the vibration device 100 may include a flexible bladder 138 connected to the body 102, the bladder is configured to be filled with a fluid. As shown in FIG. 9, in one embodiment, at least one vibration element 140 is disposed between the flexible bladder 138 and the body 102. In some embodiments, the flexible bladder 138 and at least one vibration element 140 may be connected to a body 102, including a helmet 150. Alternatively, the body 102 may include a cap. The body 102 may be made of any appropriate material, wherein one embodiment may include leather. In other embodiments, the body 102 may be made, in whole or in part, of metals, polymers, fabrics, or other suitable materials.

Referring to FIG. 7, the body 102 may include a headband 152 to be worn around a user's head. In one embodiment, the headband 152 is secured to a user's head using an adjustable strap 128. The adjustable strap 128 may be made of material that stretches or may be made of material that is rigid. In other embodiments, the headband 152 may be secured using an adjustable strap 128 and then further fitted by pressurizing or depressurizing the flexible bladder 138. A user may secure the headband 152 to the user's head with the strap 128, and then may inflate the bladder 138 using a pump 142 to fill the bladder with fluid, such as air. Upon reaching a satisfactory pressure, the user may disconnect the pump 142. In an alternative embodiment, the bladder 138 may be inflated before being secured to a user's head, and then the user or a third party may deflate the bladder 138 so as to achieve a pressure which is suitable to the user or determined by a third party, or may also be predetermined. In addition to the embodiments as described herein, prior embodiments described of the helmet 150 may also include the flexible bladder 138 connected to the body 102 as shown, for example, in FIG. 1.

In some embodiments, the bladder 138 may be filled with a fluid, for example, a gas. Alternatively, the bladder 138 may be filled with a liquid, a semi-liquid, or a semi-solid. Additionally, the body 102 may contain multiple bladders which can be inflated or deflated together, or independently, depending on the user's preferences or on the type of holistic therapy that is being given.

In one embodiment, the bladder 138 is filled with air through a pump 142 which is fluidly connected to the bladder by a connection point 148. The bladder 138 may rest against a user's head so as to create pressure for securing the device 100 to the user. The pump 142 may be used to adjust the pressure in the bladder 138 so as to reach a pressure that is determined by the user, a third party, or is predetermined. In alternative embodiments, the bladder 138 may be inflated or deflated to increase or decrease, respectively, the vibrational intensity of the at least one vibration element 140 as felt by the user through the bladder. The pump 142 may be manually actuated or may be electrically operated. Further, the pump 142 may be disposed on the body 102 or may be remote from the body.

In certain embodiments, a controller 144 may be electrically coupled to the pump 142 so as to operate the pump. The controller 144 may be the same as the controller 110 discussed above, or it may be a different or additional controller. The controller 144 may be used to turn the pump 142 on and off, or may be used to set a given pressure within the pump so as to fill the bladder 138 to a given inflated state. Additionally, the controller 144 may also be used to control the vibration characteristics. In another embodiment, the pump 142 may be configured to remove at least a portion of the fluid in the bladder 138. The pump 142 may remove a certain portion of the fluid so as to have the bladder 138 configured to an inflated state determined by the user, a third-party, or it may be predetermined.

In one embodiment, a release valve 146 may be fluidly connected to the flexible bladder 138. The release valve 146 may allow for the manual release of the fluid within the bladder 138. A user may operate the release valve 146 via a release valve button 154 to release all or a portion of the fluid within the bladder 138. In one embodiment, the user may inflate the bladder 138 to a maximum pressure, and then may use the release valve button 154 to release a portion of the fluid so as to achieve a given pressure which may be determined by the user. Alternatively, the desired pressure may be determined by a third-party.

In another embodiment, the release valve 146 may be electrically triggered so as to allow all or a portion of the fluid to be released. Additionally, the release valve 146 may also be automatically triggered upon a desired pressure of the bladder 138 being reached. The desired pressure may be determined by the user, a third-party, or be predetermined. The triggering of an automatic release valve 146 would further keep the bladder 138 from becoming over-pressurized and within a safe operating range.

Figure 10:
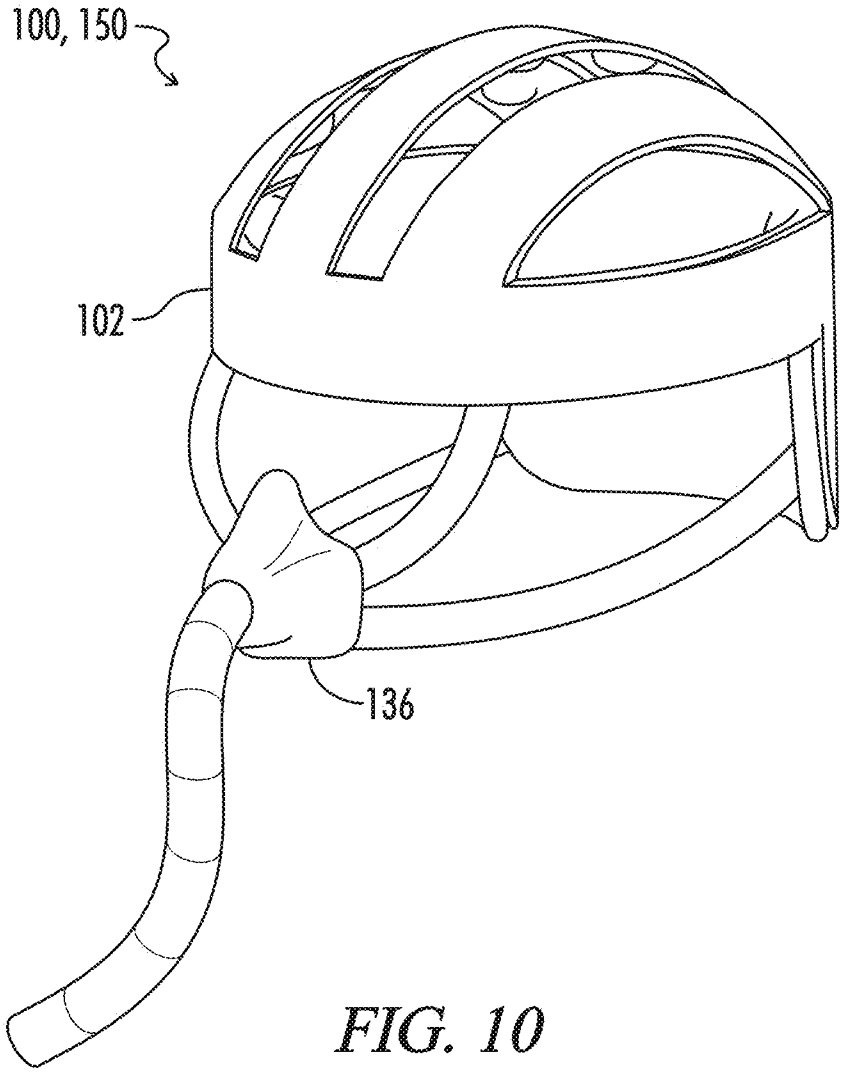
FIG. 10 is a perspective view of an embodiment of the therapeutic vibration device as a helmet including a CPAP mask attachment.

Referring now to FIG. 10, in an alternative embodiment, the vibration device 100 may further comprise attaching a continuous positive airway pressure (CPAP) mask 136 to the body 102. The CPAP mask 136 may be mounted to the body 102 through adjustable straps which allow the user to adjust the mask for comfort. Alternatively, the CPAP mask 136 may be mounted in such a way as to be detachable allowing the device 100 to be worn with or without the CPAP mask 136.

In other embodiments, additional devices, or accessories, may be attached to the vibration device. For example, a neck roll may be attached to the back of the device which provides comfort while resting the user's head against a flat surface, such as lying on a bed or while sleeping. In addition to a CPAP mask attachment, a similar BiPAP apparatus may be attached to the vibration device 100.

In addition to the foregoing embodiments disclosed above, additional embodiments as shown in FIGS. 15-21 are disclosed herein for providing vibration therapy to an individual. In certain embodiments, the therapeutic vibration device 100 may include a headset 160 capable of receiving vibrating or pulsing oscillations from an external vibration-generating source 190 (see FIG. 22). The headset 160 may be configured such that it is securable to an individual's head and may be adjustable to fit different sizes and shapes of individuals. In some embodiments, the headset 160 may be made of a rigid and/or flexible material including polymer, foam, rubber, laminates, elastomers, and the like, including combinations thereof. In certain embodiments, a portion of the headset 160 may be of a more rigid construction and another portion may be of a less rigid construction. In certain embodiments, the construction of the headset 160 may include a plurality of layers such that one layer has a lower Young's modulus than the one or more other layers. In one example, the interior side 170 of the headset 160 may be made of a material with a lower Young's modulus such as polymers, foam, rubber, and the like. The exterior side 172 may be made of a material with a higher Young's modulus than the interior side 170, such as a polymer, foam, rubber, elastomer, or composite material that has a higher stiffness to provide more durability and protection on the exterior surface. The interior surface may be made of a softer, more flexible material to allow for a more comfortable fit to the individual's head. Other layers may be included between various layers and may be of different moduli and other characteristics dependent on the application of the headset to the individual.

In certain embodiments disclosed herein, the headset 160 may include a body 162 wherein the body includes a webbed frame 163 having a plurality of interconnected beams 164 to create the headset portion for securing to an individual's head. The body 162 may further include a plurality of nodes 166 spaced along the webbed frame 163. At least a portion of the plurality of nodes 166 are positioned at predetermined locations on the interconnected beams 164 to correlate with specific locations relative to the individual's brain regions. For example, two nodes 167, 168 may be positioned at the front of a user's head for facilitating vibrations or pulsing oscillations to the frontal lobe. Additionally, other nodes may be positioned at a location adjacent the temporal lobe, cerebral cortex, parietal lobe, and/or occipital lobe. It will be understood that specific areas may be targeted for therapy and the webbed frame 163 can be configured to position one or more nodes about the target area. As used herein, the term "node" may be understood to include a position along the beam of the webbed frame corresponding to a specific target position on a user's head for therapeutic activity.

Figure 20:
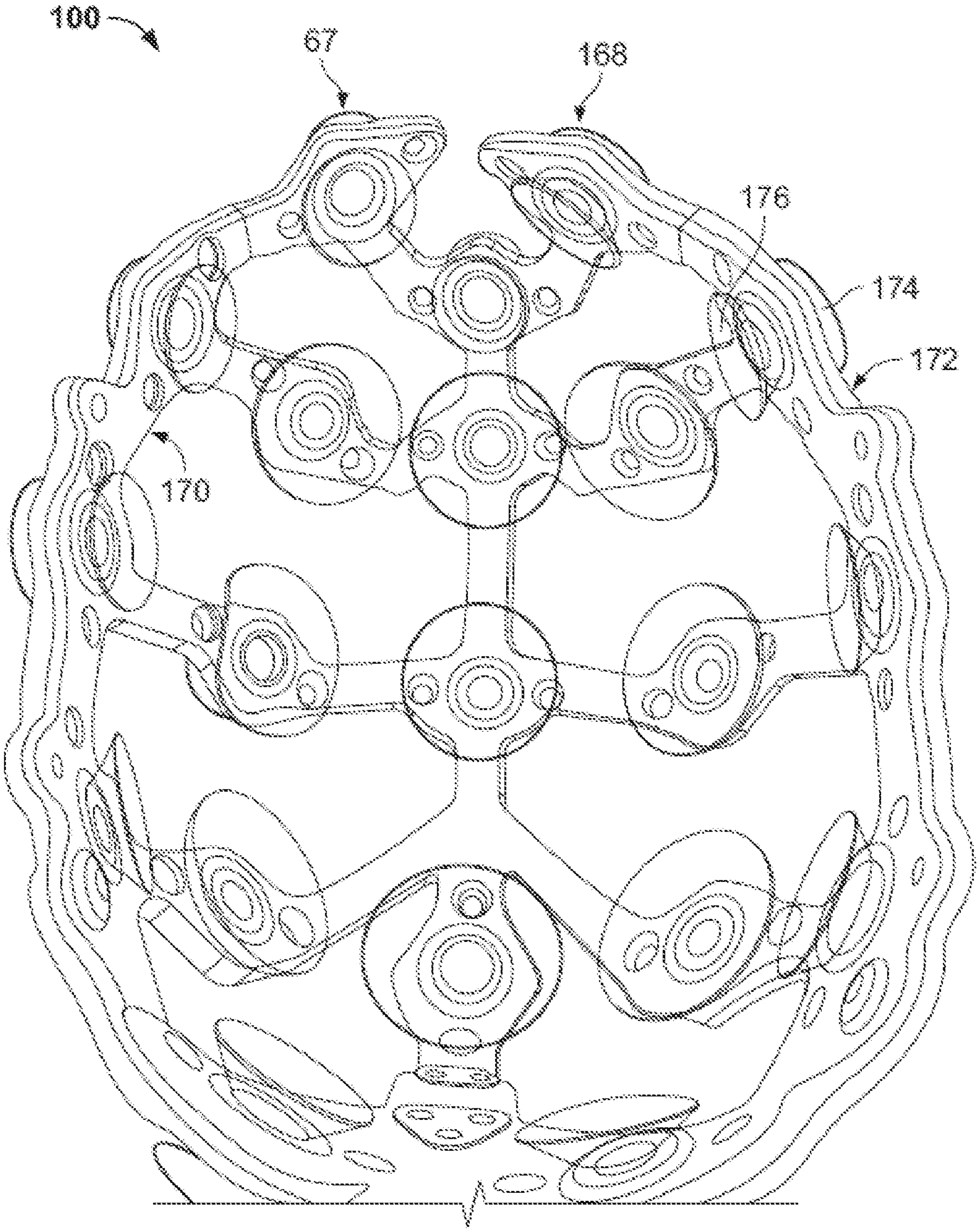
FIG. 20 is a close-up bottom view of an embodiment of a therapeutic headset with a webbed framework and internal mating members.
Figure 21:
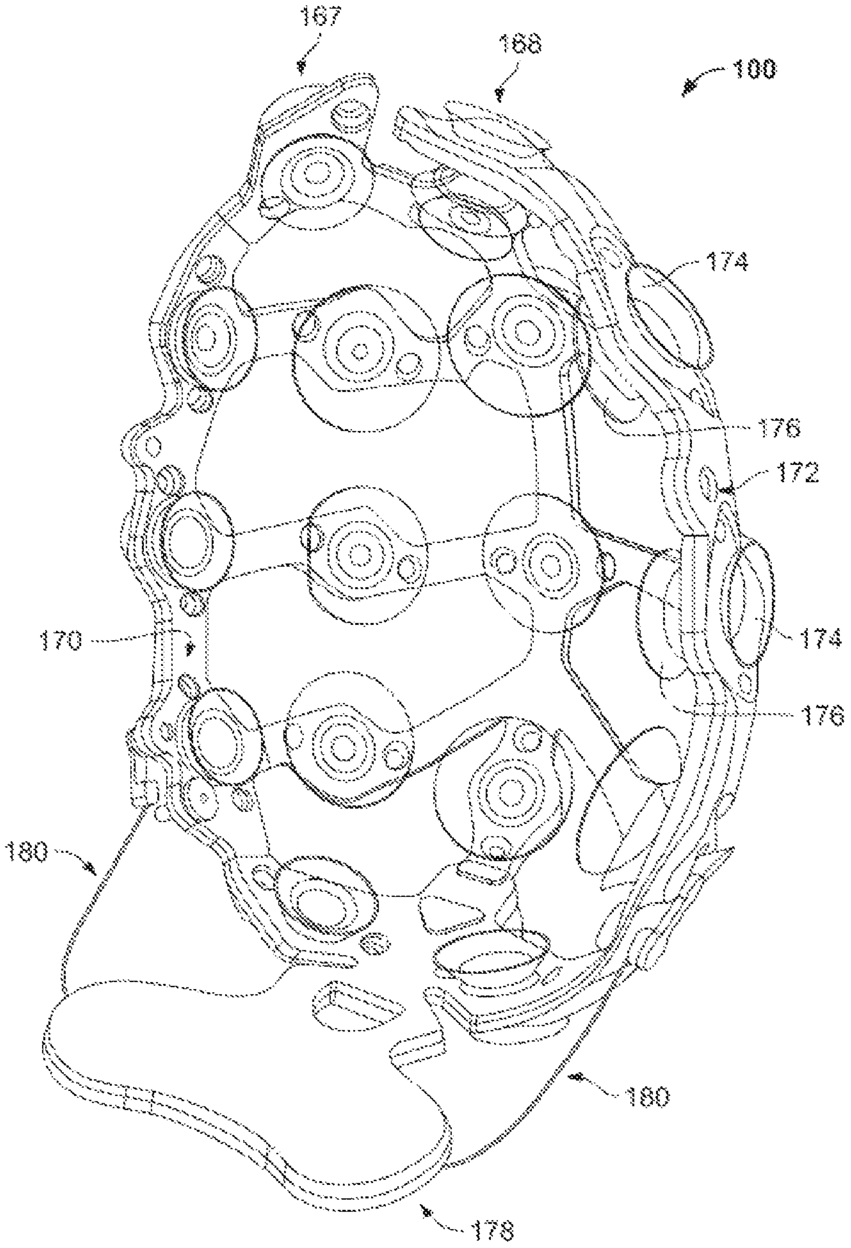
FIG. 21 is a perspective view of an embodiment of a therapeutic headset with a webbed framework and internal mating members.

The body 162 of the headset 160 may further include an interior side 170 that is positioned closest to the individual's scalp when the headset is positioned about the individual's head, and an exterior side 172 that faces away from the individual's scalp (see FIGS. 20, 21). Each node may contain an external mating member 174, an internal mating member 176, or both (see FIGS. 15, and 20-21). In some embodiments, the external mating member may be capable of mating to the vibration-generating source 190. In some embodiments, the vibration-generating source 190 may releasably couple to the external mating member 174 by mechanical means. In said embodiments, the releasable coupling may occur through a mechanical device such as a clip, fastener, clamp, retainer, pin, and the like. In other embodiments, the vibration-generating source 190 may mate with the external mating member 174 via a friction fit. In yet other embodiments, the vibration-generating source 190 may engage the external mating member 174 such that the head of the vibration-generating device 190 is "cupped" by the surface of the external mating member 174.

In certain embodiments, the external mating member 174 is configured to guide the head of the vibration-generating device 190 to contact and align the device with the preferred node 166. In one embodiment, the external mating member 174 may have a concave shape wherein the surface of the head of the vibration-generating device 190 contacts and aligns with the surface of the external mating member 174 (see FIG. 22). In certain embodiments, the external mating member 174 may have a half-sphere shape for cupping the head of the vibration-generating device 190. The advantage of such embodiments allows for the vibrating or pulsating oscillations to be directed along the node 166 of the webbed frame 163. The contact point of the head of the vibration-generating device is aligned and positioned along the node 166 and allows for a more targeted therapeutic session. Additionally, without having a cupped external mating member, the head of the vibration-generating device may be more likely to wander away from the node 166 due to the oscillations. Instead, having an external mating member as disclosed herein allows for the head of the vibration-generating device to stay in place and in contact with the node. In some embodiments, the external mating member 174 may be connected to the surface of the exterior side 172 and aligned adjacent the node 166. The external mating member 174 may be connected or fastened to the surface of the exterior side 172 such that it is permanently fixed to the surface, or is releasably fixed to the surface such that the external mating member 174 can be removable. The external mating member 174 may be made of either rigid or deformable materials. Preferably, the material may be made of a material that is elastomeric such that it may conform to the head of the vibration-generating device 190 when pressure is applied by the device, as well as limiting excess vibratory oscillations along the beams 164 and dispersing into other regions of the webbed frame 163. It is a goal of the disclosure to target the brain regions associated with each node and to limit the spread of vibratory oscillations to other regions of the brain such as when a rigid headset structure is used. By dampening and targeting the vibratory oscillations to a more targeted region, greater therapeutic outcomes can be achieved with less side effects.

In some embodiments, the headset 160 may have a plurality of nodes 166, each node having an associated external mating member 174. In some embodiments, the headset 160 may include at least 4 nodes, at least 6 nodes, at least 8 nodes, at least 10 nodes, at least 12 nodes, at least 14 nodes, at least 16 nodes, at least 18 nodes, at least 20 nodes, at least 22 nodes, at least 24 nodes, at least 26 nodes, at least 28 nodes, at least 30 nodes. In some embodiments, the headset 160 may include at least 3 nodes, at least 5 nodes, at least 7 nodes, at least 7 nodes, at least 11 nodes, at least 13 nodes, at least 15 nodes, at least 17 nodes, at least 19 nodes, at least 21 nodes, at least 23 nodes, at least 25 nodes, at least 27 nodes, at least 29 nodes. In certain preferable embodiments, the headset 160 may include 20 nodes.

In some embodiments, the headset 160 may include at least 4 external mating members, at least 6 external mating members, at least 8 external mating members, at least 10 external mating members, at least 12 external mating members, at least 14 external mating members, at least 16 external mating members, at least 18 external mating members, at least 20 external mating members, at least 22 external mating members, at least 24 external mating members, at least 26 external mating members, at least 28 external mating members, at least 30 external mating members. In some embodiments, the headset 160 may include at least 3 external mating members, at least 5 external mating members, at least 7 external mating members, at least 9 external mating members, at least 11 external mating members, at least 13 external mating members, at least 15 external mating members, at least 17 external mating members, at least 19 external mating members, at least 21 external mating members, at least 23 external mating members, at least 25 external mating members, at least 27 external mating members, at least 29 external mating members. In certain preferable embodiments, the headset 160 may include 20 external mating members.

In some embodiments disclosed herein, the internal mating member 176 may be capable of mating to the scalp of an individual's head. In certain embodiments, the internal mating member 176 may be connected to the surface of the interior side 170 of the headset 160. The internal mating member 176 may be made of either rigid or deformable materials. Preferably, the material may be made of a material that is elastomeric such that it may conform to the surface of the individual's scalp when pressure is applied by the device, as well as limiting excess vibratory oscillations to spread to other regions of the scalp and brain. The internal mating member 176 may be configured to contact the scalp and provide a rest for the device to sit on when placed on the individual's head. Additionally, the headset 160 may be configured to be adjusted for a secure fit on the individual's head, thus the internal mating members 176 may allow for comfort of the headset to be adjusted and allow for cushioning of the device as it is secured.

In one embodiment, the internal mating member 176 may have a concave shape wherein the individual's scalp contacts and aligns with the surface of the internal mating member 176. In certain embodiments, the internal mating member 176 may have a half-sphere shape for cupping the individual's scalp. The advantage of such embodiments allows for the vibrating or pulsating oscillations to be directed along the node 166 of the webbed frame 163 to the target site on the individual's brain. The contact point of the target brain region may be aligned and positioned along the node 166 and may allow for a more targeted therapeutic session. In some embodiments, the internal mating member 176 may be connected to the surface of the interior side 170 and aligned adjacent the node It is a goal of the disclosure to target the brain regions associated with each node and to limit the spread of vibratory oscillations to other regions of the brain such as when a rigid headset structure is used. By dampening and targeting the vibratory oscillations to a more targeted region, greater therapeutic outcomes can be achieved with less side effects.

In certain embodiments, the headset 160 may include at least 4 internal mating members, at least 6 internal mating members, at least 8 internal mating members, at least 10 internal mating members, at least 12 internal mating members, at least 14 internal mating members, at least 16 internal mating members, at least 18 internal mating members, at least 20 internal mating members, at least 22 internal mating members, at least 24 internal mating members, at least 26 internal mating members, at least 28 internal mating members, at internal 30 external mating members. In some embodiments, the headset 160 may include at least 3 internal mating members, at least 5 internal mating members, at least 7 internal mating members, at least 9 internal mating members, at least 11 internal mating members, at least 13 internal mating members, at least 15 internal mating members, at least 17 internal mating members, at least 19 internal mating members, at least 21 internal mating members, at least 23 internal mating members, at least 25 internal mating members, at least 27 internal mating members, at least 29 internal mating members. In certain preferable embodiments, the headset 160 may include 20 internal mating members.

In certain embodiments, the node may include an aperture that connects the surface of the exterior side to the surface of the interior side. In some embodiments, the external mating member 174 and internal mating member 176 may be a single piece that passes through the aperture and is held in place at the node 166. In some embodiments, the mating members 174, 176 may be two-piece, or multi-piece components that pass through the aperture and connect to each other. In yet other embodiments, the node 166 may be solid, but may have components for connecting the internal mating member 176 and external mating member 174 to the node. For example, the node 166 may include a means for snapping the internal mating member 176 and/or the external mating member 174 to the node. In other embodiments, the mating members 174, 176 may be slid and locked into place, or may be releasably connected in other means to the node. In certain embodiments, the mating members 174, 176 may be permanently affixed to the node via adhesive, thermoplastics, curable materials (whether radiation, moisture, or chemical-cured), or the like. In certain embodiments, the internal mating member 176 and/or external mating member 174 may be integral to the beam 164.

In certain embodiments, as shown in FIGS. 16, 19, 21, 22, the headset 160 may include a rear flap 178 capable of adjustment and securing the headset to an individual's head. The rear flap 178 may be capable of biasing the rear flap and the headset 160 to the individual's head. In certain embodiments, the rear flap 178 is connected to a beam 164 of the webbed frame 163. In some embodiments, the rear flap 178 is separate from the headset 160, but is releasable engaged with the headset such that the rear flap and headset can be biased toward or away from each other. In some embodiments, the headset 160 may include a plurality of rear flaps 178. In some embodiments, the rear flap 178 may include one or more nodes associated with the rear flap and further includes an interior side and exterior side such as disclosed above. Further, in yet another embodiment, the rear flap 178 may include one or more external mating members 174 and/or internal mating members 176 as disclosed above. Similar to the construction of the headset, the rear flap 178 may be constructed of any suitable material and may be rigid or flexible. In some embodiments, the rear flap 178 material may be of flexible material including polymer, foam, rubber, laminates, elastomers, and the like, including combinations thereof. As disclosed above, the rear flap 176 may be made of a single material, or may be made of a plurality of materials with different stiffnesses and layers as required based on the application of the headset to the individual. In certain embodiments, the rear flap 176 may include one or more tethers 180 for tethering a portion of the rear flap to the body 162 (see FIGS. 16, 19, 21, 22). A tether 180 may have a first end being coupled to the rear flap 178 and a second end being coupled to a beam 164 on the body 162. In some embodiments, the tether 180 may be capable of being pulled through a locking mechanism associated with the headset 160 such that the tether biases the rear flap against the individual's head and can be adjusted for comfort. In certain embodiments, the locking mechanism may be a dial that can be twisted to pull the tether 180 and bias the rear flap against the individual's head.

It may be appreciated that in certain embodiments, the headset 160 may be made of a single component construction such that the webbed framework is created from a single piece of material. Each beam of the webbed framework may be cut out such that void spaces are created between individual beams. This can help reduce weight of the headset. Additionally, when a layered construction is used, each layer may be made from a single piece of material, and then each piece of material is layered on the other such that a layered construction is achieved while the outer and/or inner surface is maintained with no breaks along the surface. In other embodiments, the headset may be made of multiple components joined together. In certain embodiments, one or more beams may be added to a backbone to create the webbed framework. Again, this construction may also be implemented with multiple layers of material such that each beam and the backbone are constructed with multiple layers and joined together.

Figure 22:
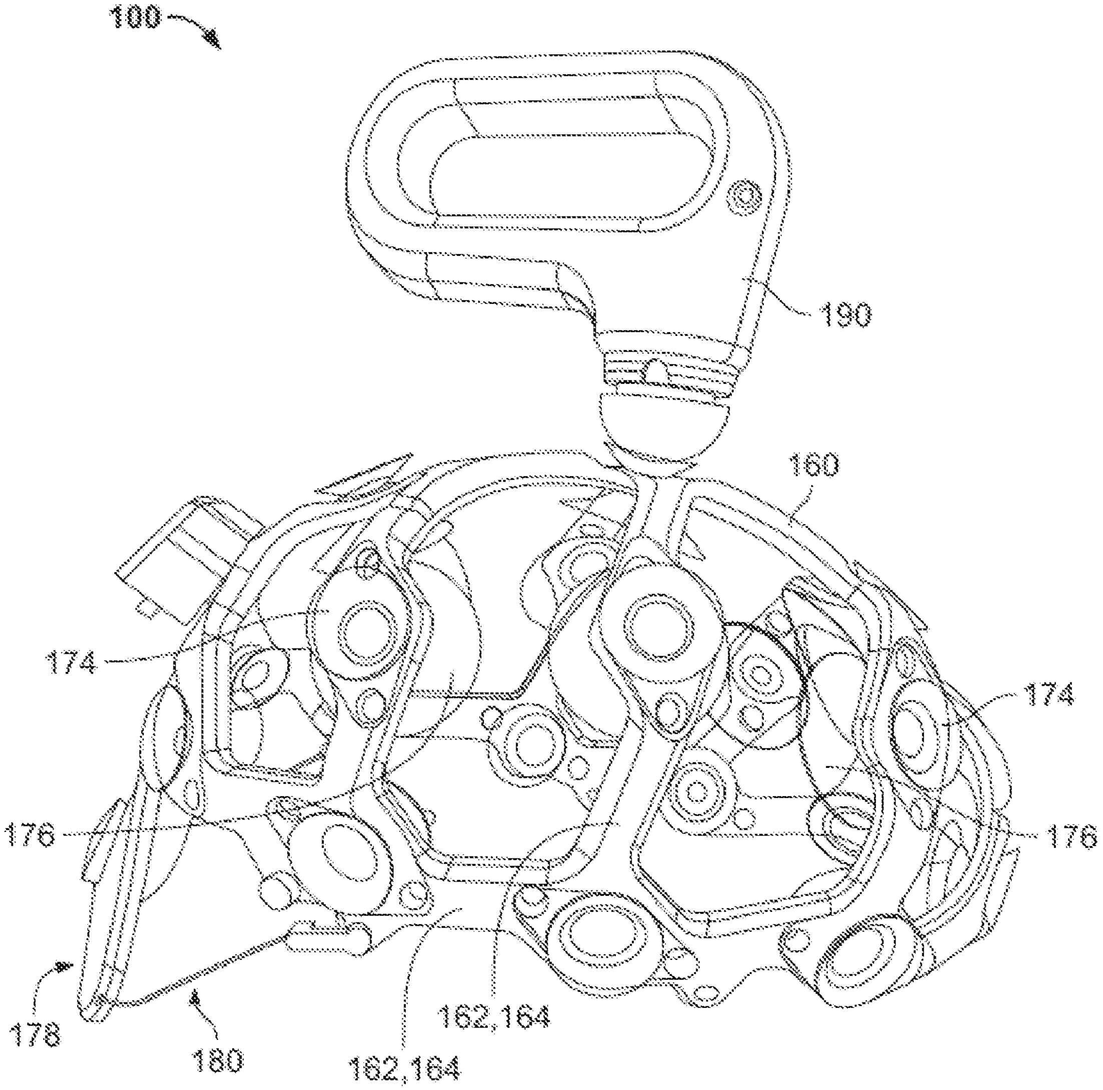
FIG. 22 is a side view of an embodiment of a therapeutic headset with a webbed framework and external mating members and a vibration-generating device mated with one of the external mating members.

Referring to FIG. 22, the vibration-generating device may be an external device that is separate from the headset 160. In some embodiments, the vibration-generating device may be a device the same as or similar to a massage gun, muscle therapy gun, and the like. The device may be capable of generating vibrating or pulsing oscillations and transmit those through a head component. The head may be of any suitable shape, including, but not limited to a sphere, ball, half sphere, cone, pronged, multi-pronged, pointed, circular, flat, wedge, and the like. In certain embodiments, the head of the vibration-generating device is configured to be mateable to the external mating member of the headset.

In certain embodiments, the vibration-generating device may be integral to the headset 160 such that one or more vibration-generating devices are located at one or more of the nodes 166. In certain embodiments, where a vibration-generating device is located on, or fixed to, the headset 160, an external mating member 174 may be unnecessary and may be absent from the embodiment.

Figure 11:
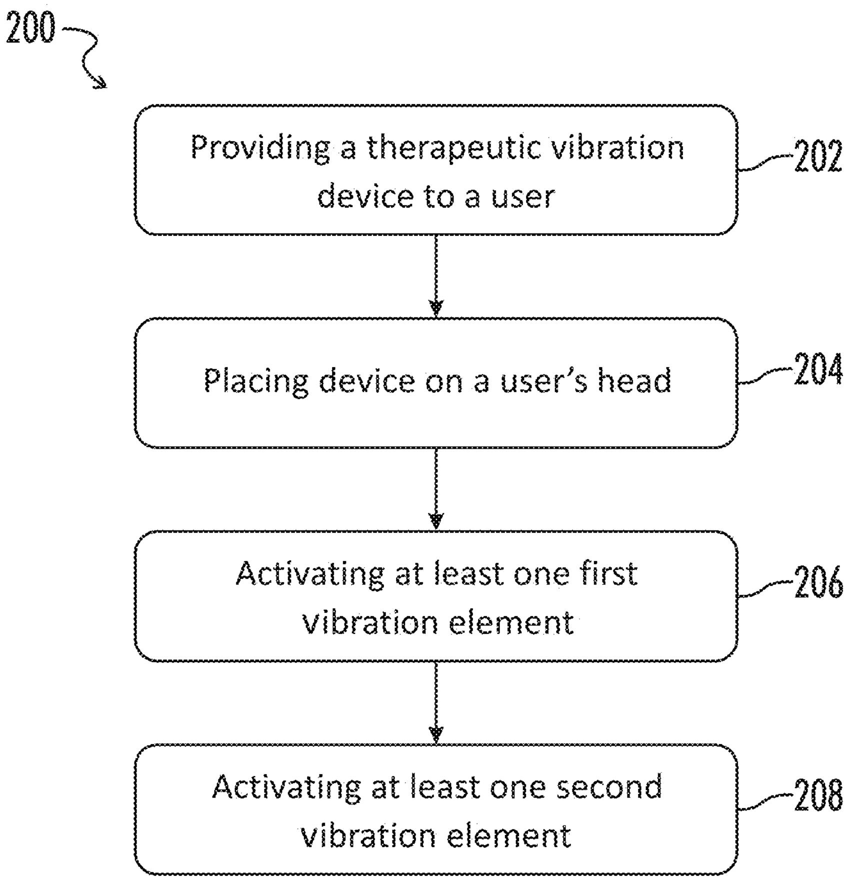
FIG. 11 is a flow chart representing an embodiment of a method for activating at least one vibration element.

FIG. 11 is an embodiment of a method for providing therapeutic vibration in accordance with the present disclosure. The method 200 may begin at step 202 by providing a therapeutic vibration device 100 to a user, then in step 204 placing the device on the user's head. In step 206, at least one first vibration element 104 is activated. The first vibration element 104 may have a first vibration characteristic including, but not limited to, vibration frequency, amplitude, or duration. In other embodiments, step 208 may be accomplished by activating at least one second vibration element 106. The second vibration element 106 may have a second vibration characteristic including, but not limited to, vibration frequency, amplitude, or duration. Further, the second vibration characteristic may be different from the first vibration characteristic as discussed above.

Figure 12:
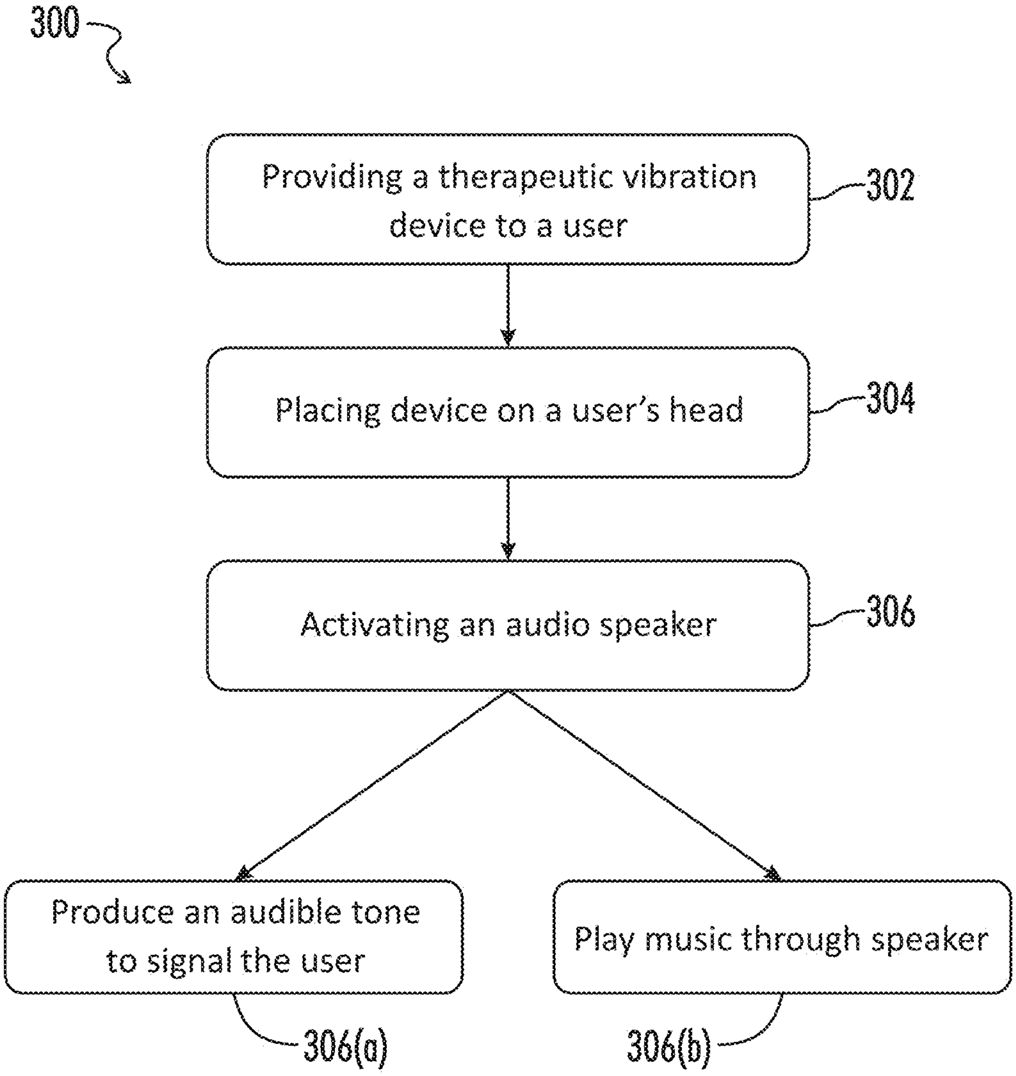
FIG. 12 is a flow chart representing an embodiment of a method for activating at least one audio transducer.

FIG. 12 is an embodiment of a method for activating an audio transducer 108 connected to a helmet 150. The method 300 may begin at step 302 by providing a therapeutic vibration device 100 to a user, then in step 304 placing the device on the user's head. In step 306, an audio transducer 108 is activated, the activation occurring independently of the at least one first vibration element 104 being activated as in step 206. In one embodiment, step 306(*a*) includes sounding an alarm to notify a user at a designated time of an occurrence of an event. For example, the transducer 108 may produce an audible tone which signals the user to switch to a different vibration pattern. In another example, the transducer 108 may produce an audible tone which signals the user to end the vibration use. Additionally, the transducer 108 may produce an audible tone which signals the user to take a medication at a certain time during the holistic therapeutic session.

In another embodiment, step 306(*b*) includes the audio transducer 108 used to play music. The music may be selected by the user, selected by a third party, or may be predetermined. The music may correspond to certain vibrational patterns or the music may be something the user finds soothing or relaxing. Additionally, the audio transducer 108 may play white noise so as to help a user fall asleep or stay asleep while undergoing holistic therapy.

Figure 13:
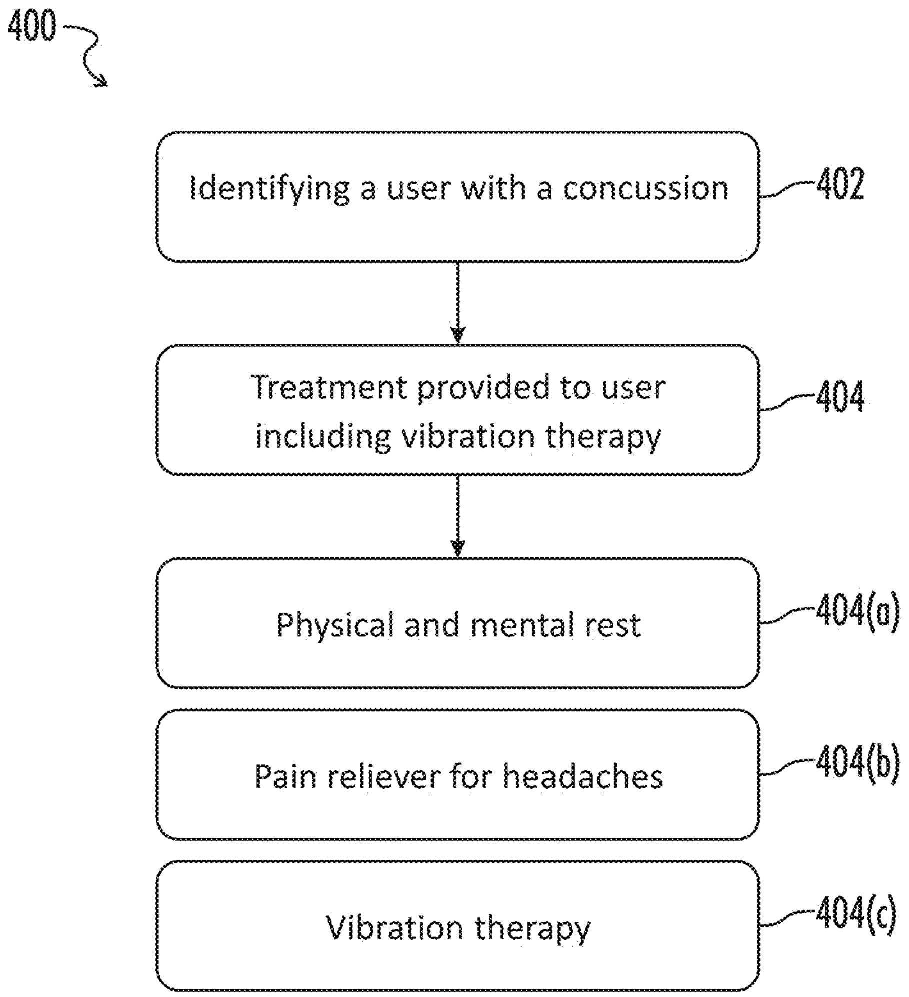
FIG. 13 is a flow chart representing an embodiment of a method for providing alternative healing to an individual with a concussion.

FIG. 13 is an embodiment for a method of including therapeutic vibration in an holistic regimen. The method 400 may begin at step 402 by identifying a user with a concussion. In step 404, the user undergoes alternative healing which includes vibration therapy. For example, a person sustaining a concussion may be treated by undergoing 404(*a*) physical and mental rest, including not doing vigorous activity, physical or mental, as well as 404(*b*) taking a pain reliever such as acetaminophen. The addition of vibration therapy to a targeted portion of the brain may be added as step 404(*c*).

Figure 14:
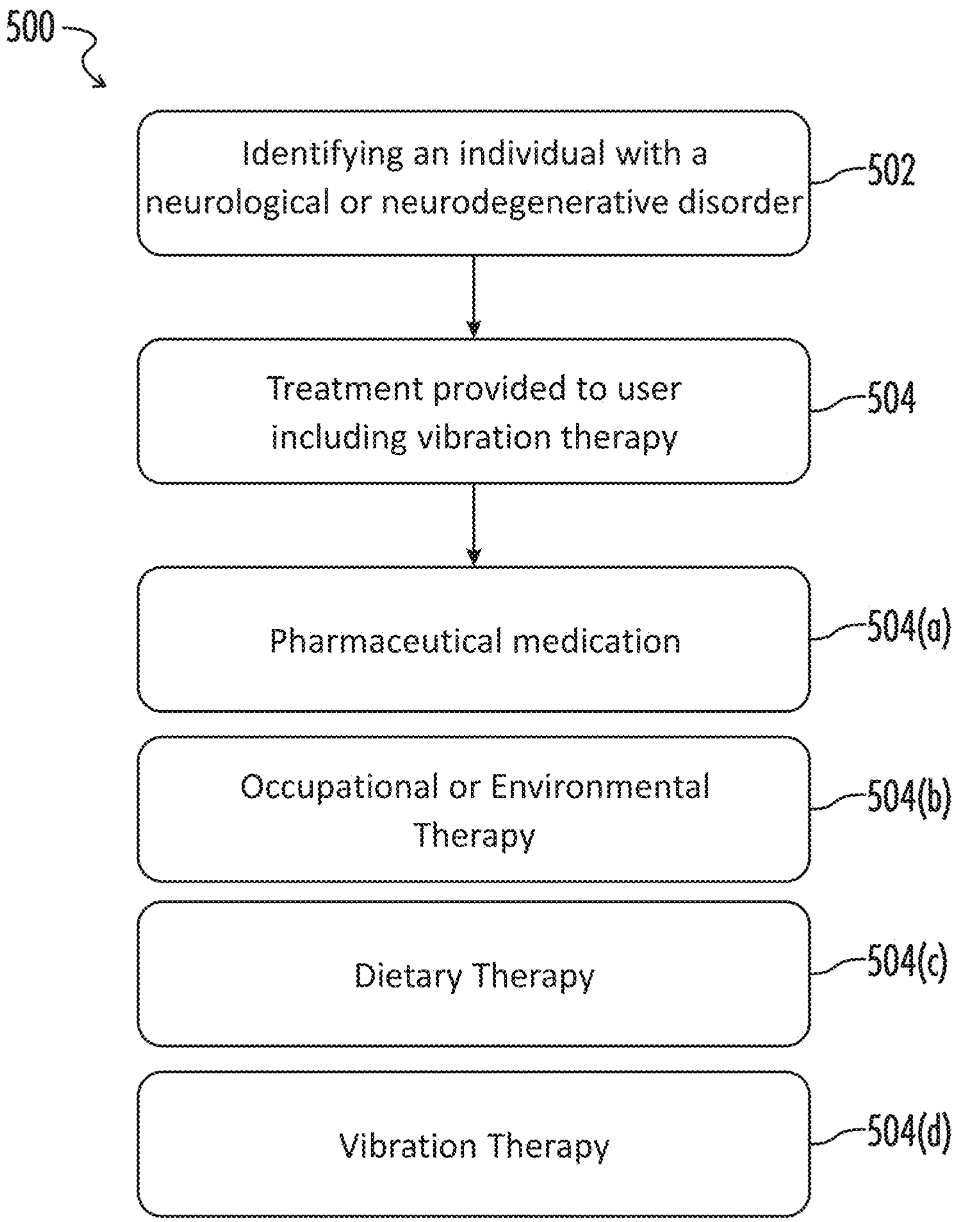
FIG. 14 is a flow chart representing an embodiment of a method for providing alternative healing to an individual with a neurodegenerative disorder.
Figure 15:
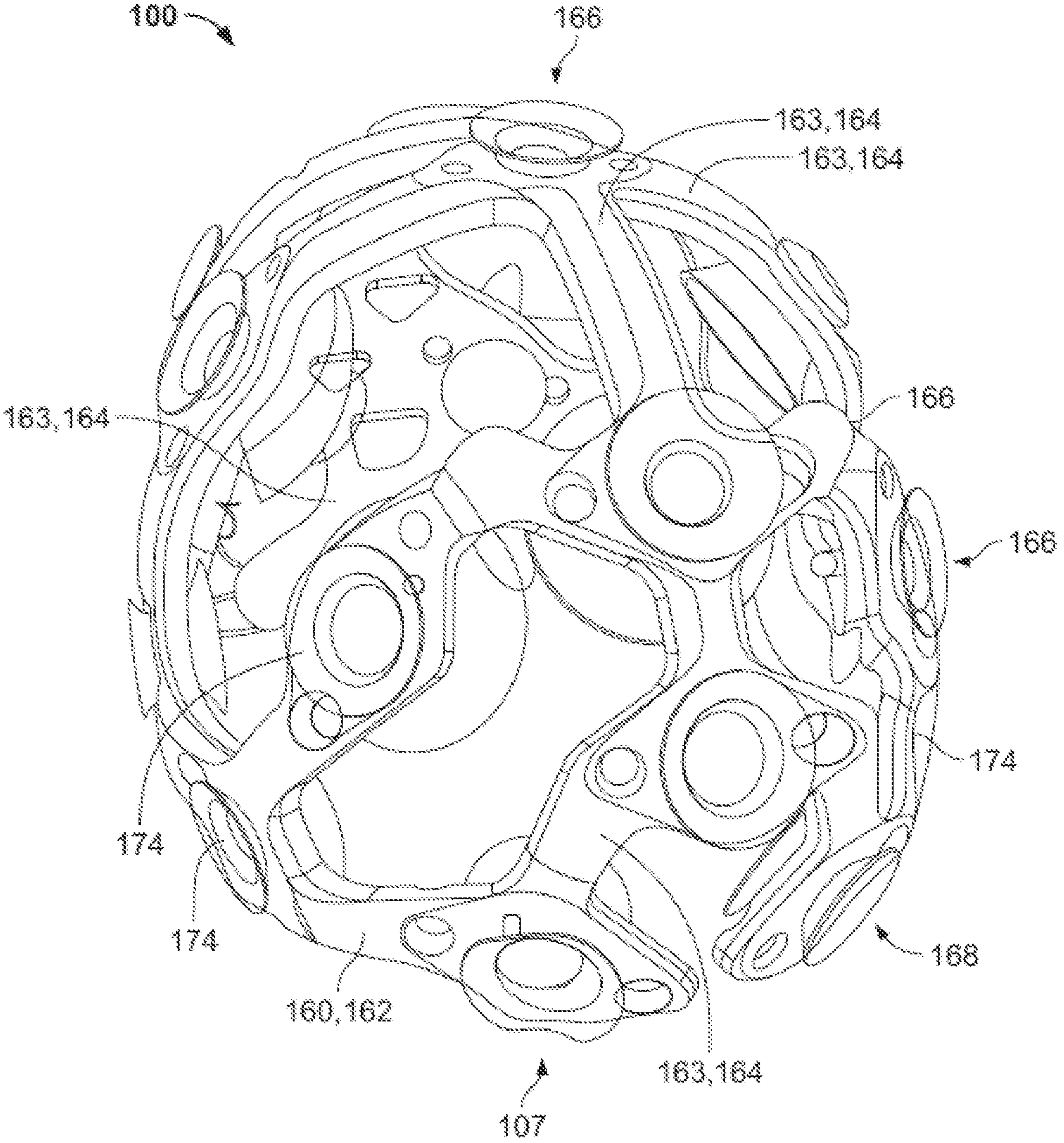
FIG. 15 is a perspective view of an embodiment of a therapeutic headset with a webbed framework and external mating members.
Figure 16:
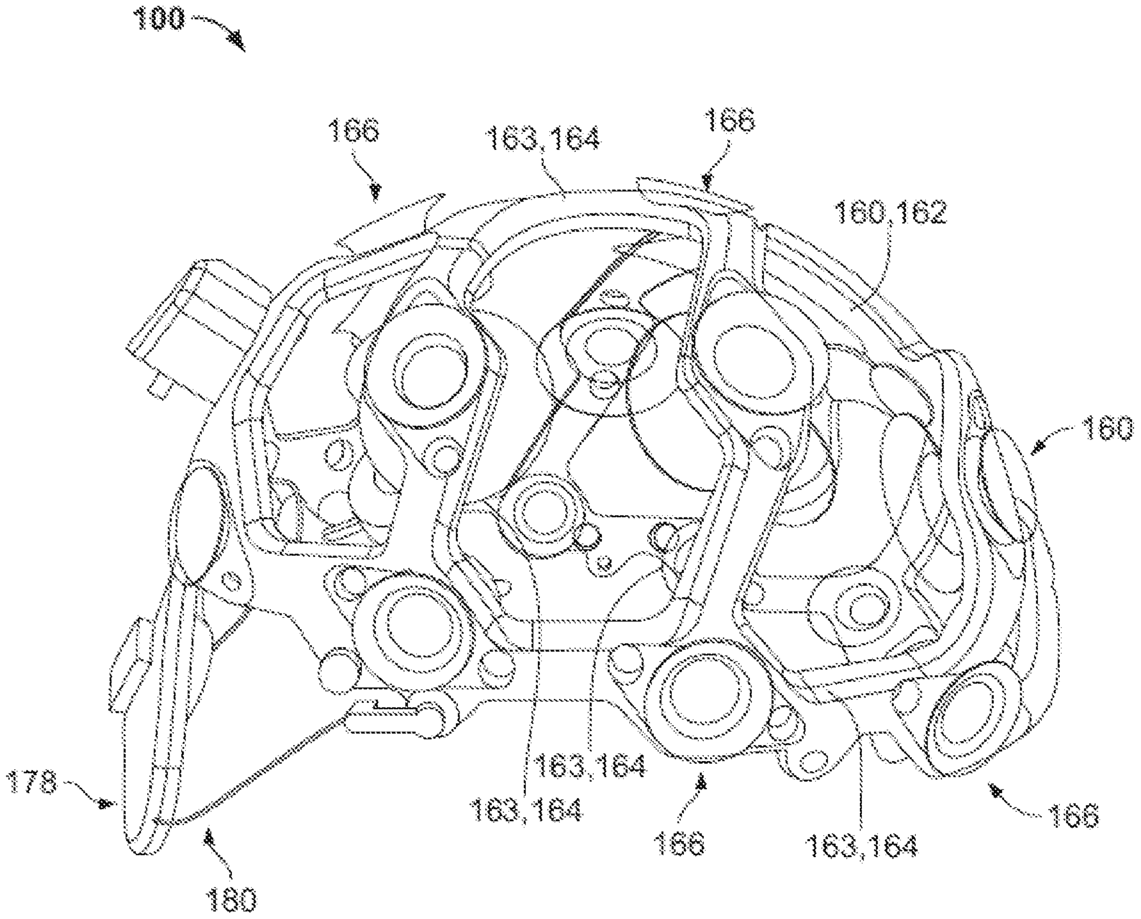
FIG. 16 is a side view of an embodiment of a therapeutic headset with a webbed framework and external mating members.
Figure 17:
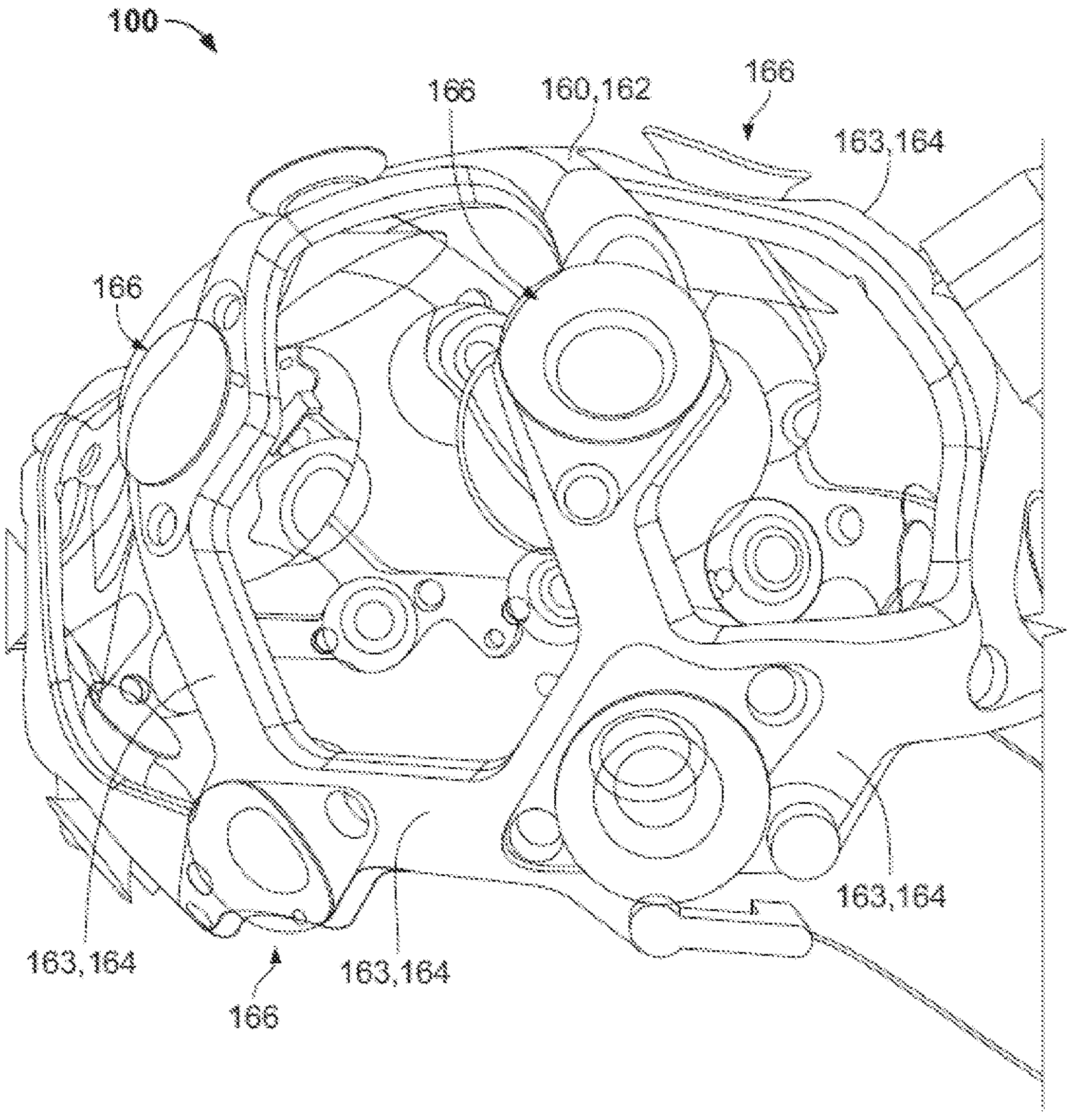
FIG. 17 is a close-up side view of an embodiment of a therapeutic headset with a webbed framework and external mating members.
Figure 18:
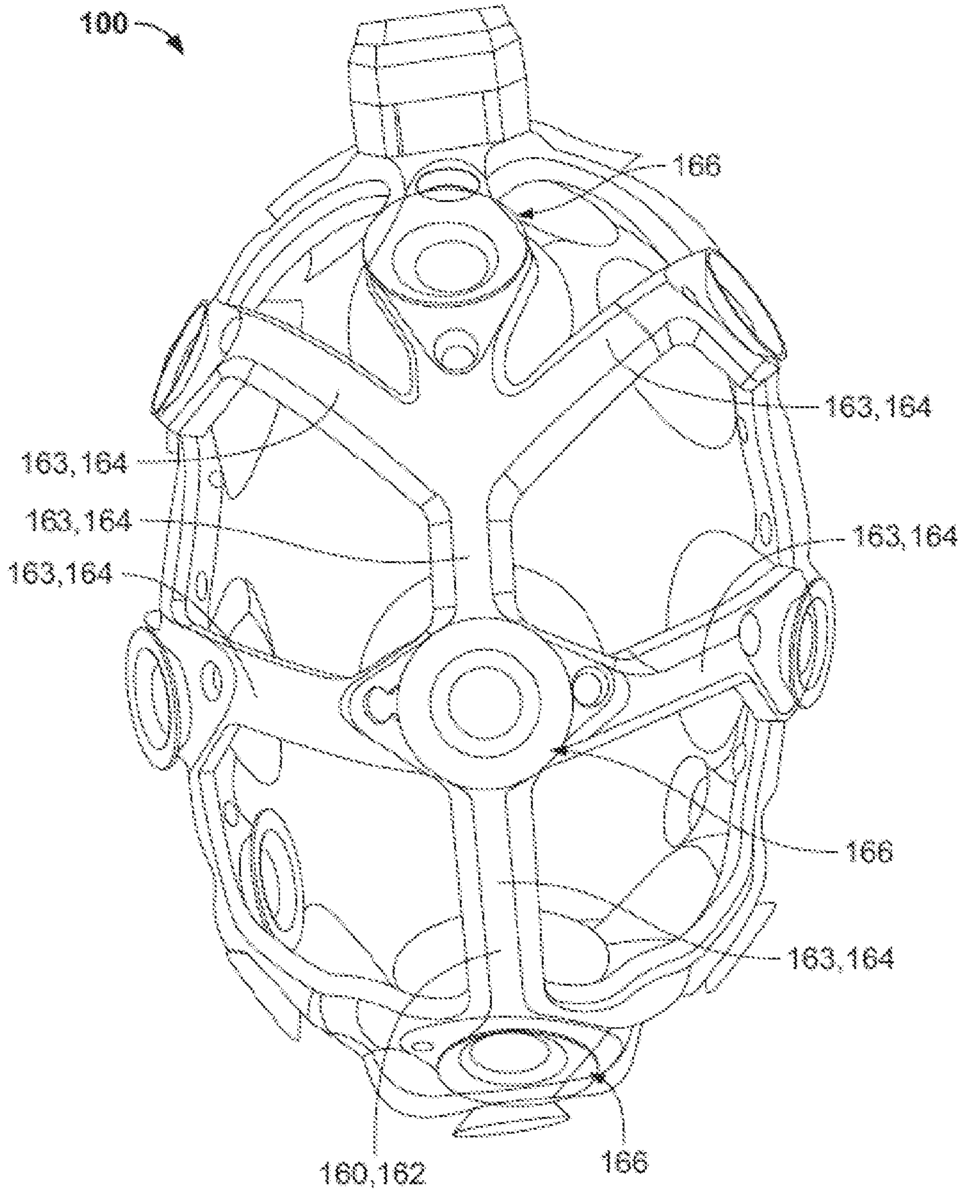
FIG. 18 is a top view of an embodiment of a therapeutic headset with a webbed framework and external mating members.
Figure 19:
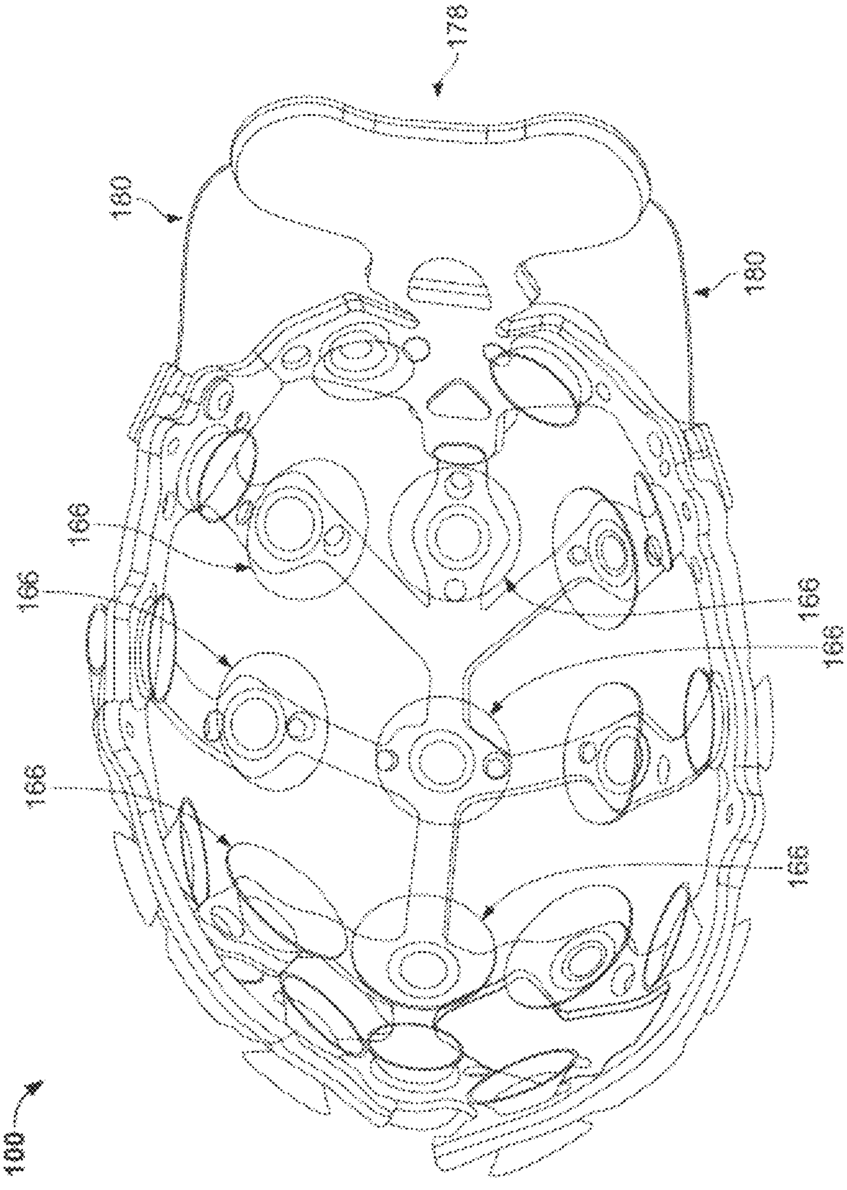
FIG. 19 is a bottom view of an embodiment of a therapeutic headset with a webbed framework and internal mating members.

FIG. 14 is an embodiment for a method of including therapeutic vibration in an holistic regimen for neurodegenerative diseases. The method 500 may begin at step 502 by identifying a user with a neurological or neurodegenerative disorder. In step 504, the user undergoes treatment for the disorder which may include alternative healing vibration therapy. As one having skill in the art will understand, there are many holistic regimens for a large number of neurodegenerative disorders. The addition of vibration therapy may be added to any one, or all, of these holistic regimens. For example, an individual with dementia may be treated by managing symptoms with 504(*a*) pharmaceutical medications including, but not limited to, cholinesterase inhibitors or memantine, also by undergoing 504(*b*) occupational therapy or environmental therapy, and finally including 504(*c*) dietary therapy such as increasing intake of vitamin E or omega-3 fatty acids. The addition of 504(*d*) vibration therapy to such a holistic regimen may provide additional benefits to the individual.

Thus, although there have been described particular embodiments of the present disclosure of a new and useful THERAPEUTIC VIBRATION DEVICE AND METHOD OF USE THEREOF, it is not intended that such references be construed as limitations upon the scope of this disclosure except as set forth in the following claims.

What is claimed is:

1. A therapeutic vibration device comprising:

a headset including a body configured to at least partially surround a user's head, wherein the body comprises a frame having interconnected beams;

a plurality of nodes disposed about positions of the frame, at least one node of the plurality of nodes disposed about an intersection of a first beam and a second beam, and at least one node of the plurality of nodes disposed about a middle portion of at least one beam, wherein the plurality of nodes is each individually capable of receiving vibrating or pulsing oscillations from a vibration-generating mechanism and include a first mating member and a second mating member;

the headset further comprises an interior side and an exterior side, wherein the interior side comprises the first mating member positioned at an interior side of a node of the plurality of nodes, and the exterior side comprises the second mating member positioned at an exterior side of the node of the plurality of nodes;

wherein the vibration-generating mechanism is an external device; and wherein the second mating member comprises a concave surface for receiving the vibration-generating mechanism.

2. The device of claim 1, wherein the headset is configured to be adjustably securable to the user's head.

3. The device of claim 1, wherein the headset further comprises a rigid material.

4. The device of claim 1, wherein the headset further comprises a flexible material.

5. The device of claim 1, wherein the headset further comprises a first portion that is of a rigid construction, and a second portion that is of a less rigid construction than the first portion or of a flexible construction.

6. The device of claim 1, wherein the at least one node of the plurality of nodes is configured to be positioned at a predetermined point corresponding to the user's frontal lobe, temporal lobe, cerebral cortex, parietal lobe, or occipital lobe.

7. The device of claim 1, wherein at least a portion of nodes of the plurality of nodes is configured to be at predetermined points corresponding to the user's frontal lobe, temporal lobe, cerebral cortex, parietal lobe, and occipital lobe.

8. The device of claim 1, wherein the first mating member the second mating member are releasably fastened to the body of the headset.

9. The device of claim 1, wherein the first mating member and the second mating member further comprise elastomeric material.

10. The device of claim 1, wherein the plurality of nodes is at least 8 nodes.

11. The device of claim 1, wherein the plurality of nodes is at least 16 nodes.

12. The device of claim 1, wherein the plurality of nodes is at least 20 nodes.

13. The device of claim 1, wherein the plurality of nodes is at least 28 nodes.

14. The device of claim 1, wherein the first mating member is configured to be capable of contacting the user's scalp such that the headset rests on the user's head through contact of the first mating member.

15. The device of claim 1, wherein the headset is a single piece.

16. The device of claim 1, wherein the headset is comprised of multiple pieces.

17. The device of claim 1, wherein the vibration-generating mechanism is integral to the headset.

18. The device of claim 1, wherein the headset further comprises voids located between the interconnected beams.

* * * * *